(12) United States Patent
Agrawal et al.

(10) Patent No.: US 6,255,359 B1
(45) Date of Patent: *Jul. 3, 2001

(54) PERMEABLE COMPOSITIONS AND METHODS FOR THEIR PREPARATION

(75) Inventors: C. Mauli Agrawal; Kyriacos A. Athanasiou, both of San Antonio, TX (US)

(73) Assignee: Board of Regents of the University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/996,745

(22) Filed: Dec. 23, 1997

(51) Int. Cl.$^7$ ................................... C08J 9/26; C08J 9/28
(52) U.S. Cl. ................................................. 521/64; 521/61
(58) Field of Search .................................... 521/61, 64

(56) References Cited

U.S. PATENT DOCUMENTS

| | | | | |
|---|---|---|---|---|
| 3,375,208 | * | 3/1968 | Duddy ..................... | 521/61 |
| 3,518,332 | * | 6/1970 | Sklarchuk et al. ...... | 521/61 |
| 3,536,796 | * | 10/1970 | Rock ..................... | 521/61 |
| 3,770,537 | | 11/1973 | Elton ...................... | 156/77 |
| 3,923,936 | | 12/1975 | Davis et al. ............ | 264/25 |
| 3,968,292 | | 7/1976 | Pearman et al. ....... | 428/213 |
| 4,177,228 | | 12/1979 | Prolss .................... | 264/24 |
| 4,181,983 | * | 1/1980 | Kulkarni ................ | 521/61 |
| 4,196,070 | | 4/1980 | Chao et al. ............. | 204/266 |
| 4,212,839 | * | 7/1980 | Funahashi et al. ..... | 521/61 |
| 4,294,753 | | 10/1981 | Urist ...................... | 260/112 R |
| 4,386,129 | | 5/1983 | Jacoby ................... | 428/215 |
| 4,455,256 | | 6/1984 | Urist ...................... | 260/112 R |
| 4,526,909 | | 7/1985 | Urist ...................... | 523/115 |
| 4,563,489 | | 1/1986 | Urist ...................... | 524/21 |
| 4,596,574 | | 6/1986 | Urist ...................... | 623/16 |
| 4,619,989 | | 10/1986 | Urist ...................... | 530/417 |
| 4,634,720 | | 1/1987 | Dorman et al. ........ | 521/63 |
| 4,659,470 | | 4/1987 | Caneba et al. ......... | 210/500.21 |
| 4,761,471 | | 8/1988 | Urist ...................... | 530/350 |
| 4,789,732 | | 12/1988 | Urist ...................... | 530/350 |
| 4,795,804 | | 1/1989 | Urist ...................... | 530/350 |
| 4,857,456 | | 8/1989 | Urist ...................... | 435/7 |
| 4,894,373 | | 1/1990 | Young .................... | 514/239.2 |
| 4,902,296 | | 2/1990 | Bolander et al. ....... | 623/16 |
| 4,902,511 | * | 2/1990 | Kronman ............... | 521/61 |
| 4,904,478 | | 2/1990 | Walsdorf et al. ...... | 424/468 |
| 4,911,931 | | 3/1990 | Baylink ................. | 424/606 |
| 4,916,241 | | 4/1990 | Hayward et al. ....... | 549/313 |
| 4,921,697 | | 5/1990 | Peterlik et al. ........ | 424/85.5 |
| 4,939,131 | | 7/1990 | Benedict et al. ....... | 514/102 |
| 4,942,157 | | 7/1990 | Gall et al. .............. | 514/108 |
| 4,969,906 | | 11/1990 | Kronman ............... | 623/16 |
| 4,975,526 | | 12/1990 | Kuberasampath et al. ...... | 530/350 |
| 5,102,917 | | 4/1992 | Bedwell et al. ........ | 521/61 |
| 5,162,114 | | 11/1992 | Kuberasampath et al. ...... | 424/423 |
| 5,171,574 | | 12/1992 | Kuberasampath et al. ...... | 424/423 |
| 5,286,763 | | 2/1994 | Gerhart et al. ......... | 514/772.4 |
| 5,324,519 | | 6/1994 | Dunn et al. ............ | 424/426 |
| 5,344,654 | | 9/1994 | Rueger et al. .......... | 424/423 |
| 5,366,756 | | 11/1994 | Chesterfield et al. .. | 427/2.26 |
| 5,460,621 | | 10/1995 | Gertzman et al. ..... | 604/358 |
| 5,492,697 | | 2/1996 | Boyan et al. ........... | 424/422 |
| 5,516,532 | | 5/1996 | Atala et al. ............. | 424/548 |
| 5,607,474 | | 3/1997 | Athanasiou et al. ... | 623/11 |
| 5,626,861 | | 5/1997 | Laurencin et al. ..... | 424/426 |
| 5,631,015 | | 5/1997 | Bezwada et al. ....... | 424/422 |
| 5,646,193 | * | 7/1997 | Brownescombe et al. ... | 521/64 |
| 5,817,704 | * | 10/1998 | Shiueley et al. ....... | 521/64 |

OTHER PUBLICATIONS

WPi/Derwent XP–002110811—PN US1694345 Nov. 30, 1991.

European Patent Office—Patent Abstracts of Japan—Application No. 53106728 filed Aug. 31, 1978.

WPI/Derwnt XP–002110808—PN JP55032651 Mar. 7, 1980 and JP57052897B Nov. 10, 1982.

Aspenberg, P., et al. "Bone morphogenetic protein induces bone in the squirrel monkey, but bone matrix does not" Thirty Ninth Annual Meeting, Orthopaedic Research Society 18, 101 (1993).

Ballock, T. T., et al. "Regulation of collagen expression in periosteal cells by three members of the TGF–B superfamily" Thirty Ninth Annual Meeting, Orthopaedic Research Society; 18,734 (1993).

Boehringer–Mannheim, Glowacki, J., et al. "The role of osteocalcin in osteoclast differentiation" J. Cellular Biochem. 45:292–302 (1991) Cytokines and Bone Metabolism, Gowen, ed. (CRC press, 1992).

Cook, S. D., et al. "Recombinant human osteogenic protein–1 (rhOP–1) heals segmental long–bone defects in non–human primates" Thirty Ninth Annual Meeting, Orthopaedic Research Society 18, 484 (1993).

Hunt, T. R., et al. "Healing of a segmental defect in the rat femur using a bone inducing agent (BIA) derived from a cultured human osteosarcoma cell line (SAOS–2)" Thirty Ninth Annual Meeting, Orthopaedic Research Society 18, 489 (1993).

Iwasaki, M., et al. "Bone morphogenetic protein–2 stimulates osteogenesis in high density culture of periosteum––derived cells" Thirty Ninth Annual Meeting, Orthopaedic Research Society 18, 483 (1993).

(List continued on next page.)

Primary Examiner—Morton Foelak
(74) Attorney, Agent, or Firm—Robert W Strozier

(57) ABSTRACT

The present invention involves compositions having variable permeation and/or porosity and objects made therefrom. The compositions are prepared by dispersing a pore-forming agent in a polymer matrix by agitation. The composition is density developed resulting in a variable concentration in pore-forming agent throughout the mixture through application of an external force on the mixture with or without continued agitation. The pore-forming agent is then leached from the mixture to form a polymer matrix having variable permeability and/or porosity.

23 Claims, 10 Drawing Sheets

OTHER PUBLICATIONS

Miyamoto, S., et al., "Trans–filter bone induction in monkeys by bone morphogenetic protein" Thirty Ninth Annual Meeting, Orthopaedic Research Society 18, 99 (1993).

Ripamonti, U., et al., "Induction of Bone in composites of osteogenin and porous hydroxyapatite in baboons" J. Plastic and Reconstructive Surg. 89:731–739 (1991).

Ripamonti, U., et al. "Initiation of bone regeneration in baboons by osteogenin, a bone morphogenetic protein" Matrix;12:40–55 (1992).

Ripamonti, U., et al. "Xenogeneic osteogenin and demineralized bone matrices including human induced bone differentiation in athymic rats and baboons" Matrix 11:404–411 (1991).

Yasko, A. W., et al. "Comparison of recombinant human BMP–2 versus cancellous bone to heal segmental bone defects" Thirty Ninth Annual Meeting, Orthopaedic Research Society 18, 100 (1993).

* cited by examiner

PERMEABLE COMPOSITIONS AND METHODS FOR THEIR PREPARATION

RELATED APPLICATIONS

This application is related to co-pending U.S. patent application Ser. No. 08/996,708 filed Dec. 23, 1997.

BACKGROUND OF THE INVENTION

1. Field of the Invention

The present invention relates to compositions having variable, controllable or differential porosities and/or permeabilities, methods for preparing such compositions and method for the use of such compositions as membranes, filters or the like.

More particularly, the present invention relates to polymeric compositions having a desired permeability and/or porosity or a desired variation in permeabilities and/or porosity where the compositions are made by dispersing one or more (at least one) pore-forming agent in a polymer matrix, optionally force developing gradients in concentrations of the agents in the composition and subsequently leaching the dispersed agents from the matrix to form the composition and methods for using the compositions.

2. Description of the Related Art

Porous and/or permeable polymeric materials find application in a wide range of applications including permeable and semi-permeable membranes, filters, biomedical applications, chromatography media, and other applications where porosity and/or permeability are characteristics that effect the performance of a given material in a given application.

Several patents have dealt with synthetic composition and articles made therefrom that related to membranes, implants or other porous and/or permeable compositions including the United States Patents described herein.

U.S. Pat. No. 5,102,917 discloses a porous polysulfone membrane made by blending polysulfone with a particulate solid or with the particulate solid and a second polymer, extruding the resultant blend to form an article and leaching the particulate solid and second polymer from the article and is incorporated herein by reference.

U.S. Pat. No. 4,969,906 discloses a microporous implant comprising a hydrophilic polymeric material having pores where the pores are formed by: (a) dispersing water-dissolvable salt in the monomer; (b) polymerizing the monomer; (c) subjecting the resulting polymeric material with salt crystals dispersed therein to an aqueous solution; and (d) shaping said polymeric material and is incorporated herein by reference.

U.S. Pat. No. 4,634,720 discloses a process for the preparation of a composite material by polymerizing in situ an N-carboxyanhydride of an a-amino acid in the presence of a powdered calcium phosphate biomaterial where the polymerization taking place in an inert organic solvent and is incorporated herein by reference. The process also includes the additional step of adding a pore-forming agent to the composite material.

U.S. Pat. No. 4,386,129 discloses a porous film made by a process comprising the steps of: (a) dispersing in a resinous polymer, a nucleating agent capable of producing beta-spherulites; (b) forming by extrusion a film with a thickness from the molten product of step (a); (c) cooling the film below the crystallization temperature of the polymer to form beta-spherulites; and (d) removing the beta-spherulites from the cooled film product of step (c) by an extracting solvent to form the porous film product and is incorporated herein by reference.

U.S. Pat. No. 4,196,070 discloses a method for forming a microporous fluorocarbon sheet membrane comprising: (a) mixing an aqueous dispersion of fluorocarbon polymer with a pore-forming agent comprising a water-soluble crystallizable metallic organic salt; (b) forming a wet sheet from the aqueous dispersion; (c) concentrating the aqueous dispersion; (d) drying the crystal-containing sheet; (e) sintering the dry sheet; and (f) leaching the salt crystals from the sheet in an aqueous medium and is incorporated herein by reference.

U.S. Pat. No. 3,770,537 discloses a method of making a microporous film comprising: grinding a milled mixture comprising a thermoplastic polyurethane resin and a plurality of water-soluble particles; heat-forming the ground mixture to form a film; heat treating the film under a pressure of less than 10 p.s.i.; and leaching said particles from said heat-formed film and is incorporated herein by reference.

Although these patents relate generally to microporuos film, there is still a need in the art for cost effective and efficient methods for making polymer compositions that have controlled permeability and/or porosity or controlled variable permeability and/or porosity.

SUMMARY OF THE INVENTION

The present invention provides polymer compositions having a desired degree of permeability and/or porosity across a region or cross-section of an article made therefrom or a desired variation in permeability and/or porosity across a region or cross-section of an article made therefrom. The compositions and articles made therefrom can have permeabilities and porosities that range from substantially impermeable and/or non-porous to highly porous and highly permeable or any combination of permeability and porosity. The compositions and the articles made therefrom have potential use as separation media, open and closed foams, filters, permeable and semi-permeable membranes, implants or the like.

The present invention also provides methods for making composition having a substantially uniform, variable and/or differential permeability and/or porosity. Broadly, the method includes mixing into a polymer matrix having a first density, at least one pore-forming agent having a second density.

During or after the mixing, the agents can be allowed to anisotropically distribute throughout the polymer matrix or portions thereof due to the action of an external force such as gravity. This anisotropic distribution of agents in the matrix results in formation of compositions with variable permeabilities or porosities. After mixing and optional force development, the pore-forming agents are removed, leached or extracted from the matrix yielding a porous and/or permeable composition.

The method can also include agitating the polymer matrix containing the pore-forming agents so that void spaces formed in the polymer matrix will be generally larger than the actual physical size of the pore-forming agents, at least for solid pore-forming agents. The amplitude, direction and frequency of the agitation will control to some extent the size and shape of the void places formed in the composition after removal of the pore-forming agents. Preferentially, the mixing is carried out under controlled conditions where the controlled conditions include air-flow and optionally temperature, pressure, gas composition and/or humidity. Alternately, the mixing step can be the agitation step where the composition is mixed by vibronic agitation and not by other mixing techniques such as stirring, extruding, masticating, or the like.

Force development (anisotropic distributions of particles in the polymer matrix caused by the application of an external applied force) of the composition is preferably continued until a desired degree of variation in porosity and/or permeability is achieved. In a most severe case, one portion of the composition is rendered substantially impermeable and non-porous. Of course, combinations of force development, agitation, and mixing can be used to prepare compositions of the present invention as well with varying permeability and porosity characteristics.

This invention also provides methods for making composites having differential or variable permeability and/or porosity by adhering or affixing a first composition having a first permeability and/or porosity to a second composition having a different permeability and/or porosity. Such composites can have simple or complex differential permeabilities and/or porosities. The first and second compositions can be substantially uniform composition made by the method of the present invention or commercially available or can be different compositions of this invention having variable permeability and/or porosity.

Thus, composite structures can be prepared having complex arrays of porosities and/or permeabilities, either static or variable within regions of or throughout the entire composite structure. In fact, one part or region of the structure could allow permeation by a first class of materials, while an adjacent part or region of the structure could allow permeation by another class of materials where the classes can be disjoint (distinct) or one can include the other as a subclass.

The present invention also provides compositions having controlled, variable and/or differential permeabilities and/or porosities to fluids (e.g., liquids, solutions, dispersions, emulsions, gases or mixtures or combinations thereof) or fluid components (solutes, dissolved gases, solvents, or combination or mixtures thereof) where the permeability and/or porosity can range from substantially or essentially impermeable, impervious and/or non-porous to highly porous and/or permeable to such fluids or fluid components.

The present invention further provides methods for making the compositions having substantially uniform porosity and/or permeability invention. The method includes sequentially adding at least one pore-forming agent to a polymer solution or melt where the additions are carried out under agitation and controlled conditions where the controlled conditions are air flow and/or temperature, pressure, gas composition and/or humidity. Preferably, the last addition of the agent(s) occurs prior to complete evaporation of the solvent or cooling of the melt to ensure that the top, outer surfaces or regions of the composition have a porosity and/or permeability substantially similar to the porosity and/or permeability of the bulk of the composition and to prevent formation of a polymeric skin essentially void of solid particles. Once the composition has been formed, the composition is contacted with a leaching agent that removes the pore-forming agents from the matrix to form a composition having a desired substantially uniform, permeability and/or porosity to a given substance or class of substances throughout the entire composition.

The present invention also provides methods for making composition having substantially isotropic or anisotropic distributions of pores, pore sizes and/or pore shapes throughout the composition. The method includes the step of mixing into a polymer solution or melt having a density of $\rho_0$ at least two pore-forming agents. The agents have densities of $\rho_i$, sizes $\sigma_i$ and shapes $\phi_i$ where i is an integer representing the number of solids utilized.

Anisotropic particle distributions result from dissimilarities between the densities, sizes and/or shapes of the agents based can be induced in the composition either through the application of an external force or through the application of vibronic agitation or both. The action of the applied external force in conjunction agitation causes the agents to migrate in the composition based on their density. Thus, denser particles and more regular shaped particles tend to migrate faster than less dense particles and smaller and irregular shaped particles resulting in anisotropic distributions of pores, pore sizes and pore shapes throughout the composition. The applied force can be gravity or gravity in combination with other applied forces such as centripetal force, magnetic force (for particles having susceptibility to magnetic forces), electric force (for particles having susceptibility to electric forces) or other applied forces. For vibronic agitation such as ultrasonic or mechanical vibratory excitation, the amplitude, direction and frequency of the agitation can affect particle distribution and the size and/or shape of a cavity produced in the polymer matrix during agitation.

Furthermore, the compositions of this invention can be formed not only with variable permeability and/or porosity as to a concentration of pores or void regions having one given size and/or shape, but also with variable permeability and/or porosity where the concentration of pores, pore sizes and/or pore shape and therefore the permeability and porosity can vary across a given profile of an object or portion(s) thereof.

Moreover, composite structures can also be prepared where different portions, parts, sub-structures, surfaces, regions or combinations thereof have different static or variable permeation and/or porosity so that the composite structure can be used to direct different materials or classes of materials into and out of different channels or diffusion pathways in the composite structure.

This invention further provides for methods of using the composition as filters, filtrations membranes, separation media, chromatography media, permeable and semi-permeable membranes and biomedical implants.

DESCRIPTION OF THE DRAWINGS

The invention can be better understood with reference to the following detailed description together with the appended illustrative drawings in which like elements are numbered the same.

DESCRIPTION OF THE PREFERRED EMBODIMENTS

Figure 1:
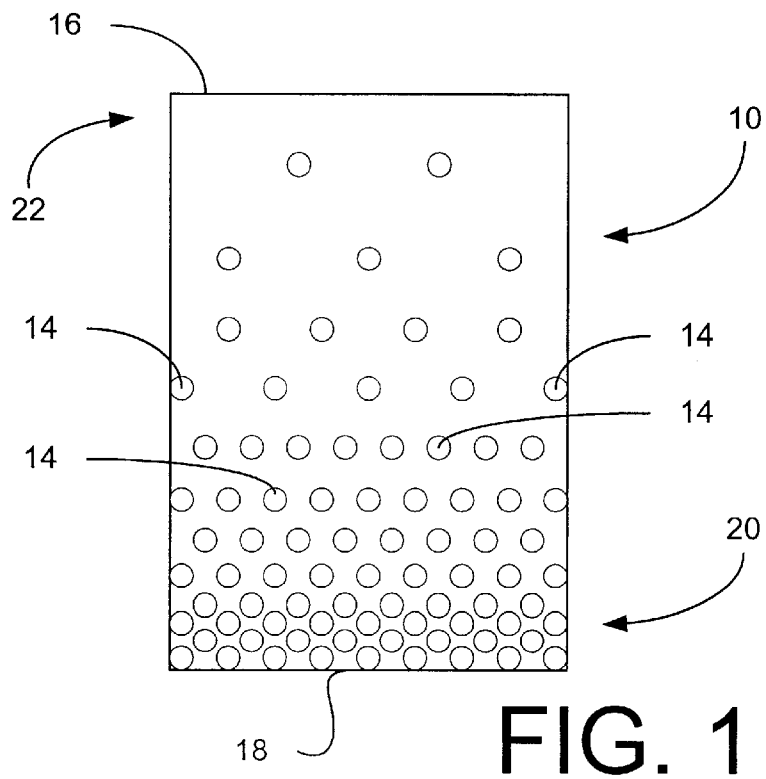
FIG. 1 is a cross-sectional view of a first embodiment of an object prepared from a composition of the present invention having a single force induced variation in permeability and/or porosity.

The inventors have found that polymer compositions having a desired degree of permeability and/or porosity or a desired variation in permeability and/or porosity can be prepared. Objects, constructs or composites composed of these compositions can have permeabilities and/or porosities that are substantially uniform or variable throughout an entire object or any region thereof. The permeabilities and/or porosities can range from essentially or substantially impermeable and/or non-porous to highly permeable and/or porous to a desired class or classes of materials. Isotropic and/or anisotropic compositions of the present invention and articles made therefrom are suitable for use in many applications such as: filters; permeable, semi-permeable or differentially permeable Ad membranes; separation media, filtration membranes, open and closed foams, implants or any other use.

Moreover, the objects can have different regions where each region has permeabilities and/or porosities that vary across a profile of the region. The variation in permeability can range from essentially or substantially impermeable to highly permeable to the same or different class of materials, while the variation in porosity can range from essentially or substantially non-porous to highly porous. Of course, very complex composite structures can be designed with very complex permeability and/or porosity behaviors.

Furthermore, the compositions of this invention can be formed not only with variable permeabilities and/or porosities resulting from concentration gradients of pores or void regions having a given size and/or shape, but also with variable permeabilities and/or porosities resulting from concentration gradients in pore concentrations, pore sizes and/or pore shapes.

Additionally, the pores can be either highly interconnected or highly disjoint. Highly interconnected pores generally yield composition with increased permeability (such as hydraulic permeability or permeability to a given class of materials), while highly disjoint pores generally yield compositions with reduced permeability for the same porosity (void volume/total volume). Of course, for objects that require permeability such as a permeable or semi-permeable membrane, then the composition will have a higher number of interconnected pores, than for an object that require a given porosity where interconnected or disjoint pores are acceptable. Obviously, for closed foams, the composition should have relatively high concentration of disjoint pores.

Composite structures can also be prepared where different portions, parts, sub-structures, surfaces, regions or combinations thereof have different static or variable permeability and/or porosity so that the composite structure can be used to direct different materials or classes of materials into and out of different channels or diffusion pathways in the composite structure.

The composition of the present invention are prepared by dispersing one or more (at least one) pore-forming agent in a polymer composition, generally a polymer melt or solution, to form a polymer matrix having the agents dispersed therein. Preferably, the agents have a density or densities different from the density of the polymer composition or the resulting polymer matrix. Because the polymer composition, into which the agents are dispersed, can be a solution or a melt, the density of the polymer matrix can change somewhat during preparation. Therefore, it is preferable that the density of each agent be different from the density of the starting polymer composition and the final polymer matrix.

The step of dispersing can be effectuated by any mixing technique including stirring, masticating, extruding, vibronically agitating or the like. In one preferred embodiment, the step of dispersing is by mechanical or sonic agitation or other similar vibronic agitation technology. In another preferred embodiment, the compositions are first mixed and then subject to vibronic agitation to augment pore size and shape in the composition.

Agitation is preferably carried out under controlled conditions where the conditions to be controlled include airflow over the surface of the mold containing the composition and optionally temperature, pressure, gas composition and/or humidity. Of course, the agitation can be carried out in a closed atmosphere where control of air flow would not be as critical. If vibronic agitation is used to mix the composition, then agitation is generally continued for a time sufficient for the pore-forming agents to be distributed in the polymeric matrix to a desired degrees of dispersion.

Air flow control is thought to control the amount and rate of solvent evaporation from a polymer solution during agitation. Uncontrolled loss in solvent via evaporation during agitation can result in incomplete dispersement in pore-forming agents and in a lack of uniformity in pore distribution whether uniform or variable.

Vibronic agitation, besides simply mixing, causes the particulate pore-forming agents to oscillate at a frequency corresponding to a frequency of the agitation. The oscillation will also have an amplitude and direction corresponding to an amplitude and direction of the agitation. This oscillation of the particles generally causing formation of a larger void volume than a volume of the particle itself, which, of course, is the minimum void volume that will ideally be left behind after particle extraction. Depending on the frequency, direction and amplitude of agitation, the voids left behind after particle extraction can be substantially spherical or non-spherical (elongate, rod-like, tube-like, irregular shaped, ellipsoidal, or the like).

Moreover, the agitation direction, amplitude and frequency can be changed during composition preparation to create any desired pore size and/or shape. Thus, one-directional agitation can cause pores to have a tubular shape, if the direction of agitation is later changed, then the pores could have an x shape. More complex shapes can be created by changing the direction, amplitude and frequency of agitation during composition preparation.

If the composition is subjected to an external force other than or in addition to agitation during preparation, then a variation in the distribution of pore-forming agent and/or the size and/or shape the resulting voids throughout the composition can be achieved. The external force can be static or variable and can be applied before, during, intermittently or after agitation. The difference in density between the polymer matrix and the pore-forming agents is what allows force developed anisotropic distributions of the agents in the polymer matrix to occur. Of course, gravity is always acting on the composition during its preparation and particle gradients induced by gravity will generally occur during any formation procedure. However, using the present method, the gradients in particle concentrations can be facilitated by either inducing a greater gravitational force or other applied forces such as centripetal force. Moreover, by applying a centripetal force directed parallel to the gravitational force, a composition can be prepared where the effects of gravity are negligible or are greatly minimized.

Centripetal force will cause a radial anisotropic distribution of the particles dispersed in the matrix with respect to an axis of rotation. The degree of anisotropy will depend on a magnitude of the centripetal force and on a period of time that the applied force acts on the composition. Other factors that control the degree and rate of segregation or anisotropic distribution of the particles include the viscosity of the polymer matrix, the temperature, the pressure, the nature of the pore-forming agents, the size and shape of the pore-forming agents if in particle form, or the like.

The compositions can also be subjected to a combination of forces so that variations in two or more dimensions can be induced in the compositions. Thus, the composition can be place in a cylindrical mold so that mold can be spun to achieve a radial anisotropic distribution of the pore-forming agents. If the cylinder is spun so that the force is not parallel to the force of gravity, then the action of the centripetal and gravitational force will induce an anisotropic distribution of pore-forming agent along two directions—one corresponding to the direction of gravity and one corresponding to the direction of the centripetal force.

The inventors have also found that compositions can be prepared with anisotropic distributions of pore sizes by using a single solid having a plurality of particles sizes and/or shapes so that vibronic agitation and/or force development act to concentrate different sizes and/or shapes of the pore-forming agents in different regions of the composition. The regions of concentration of different particles can also be influenced by the order or sequence of addition of the different particles to the composition during preparation and by the duration of agitation period after each successive addition.

Alternatively, anisotropy can be introduced into the composition by using more than one particulate materials where the materials, generally solids, have different densities and/or different particle sizes and/or different shapes. Thus, through a combination of agitation and externally applied forces such as gravity (standard or enhanced by centrifugation), centripetal force, magnetic force, electrical force or a combination thereof, the resulting compositions can be prepared with any desired anisotropic distribution of pores with one type of particle being concentrated in one region and another type of particle being concentrated in another region and so on. Of course, compositions can also be prepared where the permeability and/or porosity varies from substantially zero (to a given substance or class of substances) to highly permeable and/or porous with respect to that given substance or class of substances.

In one preferred preparation method, the inventors have also found that if the addition of particulate pore-forming agents occurs in at least two stages, then compositions with more uniform permeabilities and/or porosities with respect to each particulate material can be prepared. Generally, the first addition can comprise the addition of the bulk of the leachable, particulate materials to the polymer solution or melt, while the final addition generally comprises a smaller portion of the materials and occurs prior to complete solvent evaporation and/or matrix cooling. This final addition is designed to prevent formation of a less permeable and/or porous polymer skin on the surface of the resulting composition and to ensure that the top portion of the composition has essentially or substantially the same concentration of particles as the bulk composition. Preferably, the multi-addition of particulate pore-forming agents is carried out under vibronic agitation as the means for mixing or dispersing.

It should be recognized that non-particulate pore-forming agents and even pore-forming agents that are soluble in the polymer matrix can be used in the method of the present invention, provided that the pore-forming agent can be subsequently extracted, leached out or otherwise removed from the polymer matrix leaving behind voids or pores.

If a polymer solution is used in the methods of this invention, then during mixing, agitating and/or segregating or force developing, a certain amount of solvent will be removed from the polymer composition. Solvent evaporation is preferably controlled during mixing, agitating, and/or segregating so that variability in mixing, agitation and force development processing can be minimized—solvent loss affects the polymer viscosity and the mobility of substances and particles through the matrix.

Although some solvent is lost during mixing, agitation and/or segregation, to ensure move complete removal of solvent, the compositions are generally subjected to processes to remove or reduce the amount of solvent in the composition. Preferably, the solvent removal step include subjecting the composition to either a reduced pressure environment or heating the composition or a combination thereof for a time sufficient to ensure substantial removal of solvent. Additionally, the temperature can be held constant, then ramped to a new temperature and held, etc. with or without the composition being subjected to a reduced pressure environment.

Once a desired degree of dispersion and/or segregation or variation in the concentration of pore-forming agents in the polymer matrix has been achieved and, if necessary a desired degree of solvent removal, the composition is, then, contacted with a leaching reagent that removes the agents from the polymer matrix leaving voids or pores therein. The resulting composition will have a pore distribution (concentration, size and/or shape distribution) substantially identical to the distribution of pore-forming agents in the composition, provided the leaching agent does not adversely affect the polymer matrix by causing voids to collapse or otherwise change shape.

After leaching, the polymer material is dried for a sufficient amount of time to remove any leaching medium that may be occupying the pores. Preferably, the polymer material is air-dried for approximately twenty-four hours followed by vacuum-drying for approximately forty-eight hours. Additionally, the composition can be subject to heating during the drying or solvent removal process.

Additionally, the compositions of the present invention can be subjected to post formation (after preparation and leaching) cross-linking reactions either by chemical or physical cross-linking procedures depending on the polymers used to make the compositions and upon the application to which the compositions are to be used. Such cross-linking systems can include, without limitation, peroxide cross-linking agents, sulfur cross-linking systems, ionizing radiation, UV radiation for light curable polymers, or the like.

Of course, cross-linked compositions would generally be less susceptible to degradation. However, by subjecting regions of an implant, filter or membrane having variable permeability and/or porosity to differential cross-linking, objects can be constructed with regions designed to degrade and regions designed not to degrade. Chemical cross-lining agents can be added to the composition by dipping or soaking the composition in a solution containing the cross-linking agents where the solvent allows the crossinking agents to penetrate the polymer matrix without significantly adversely effecting the concentration and distribution of pores in the composition.

In another preferred method of this invention, at least one gas producing, pore-forming agent, generally a solid, is dispersed in the polymer matrix. After dispersing and/or force developing the composition to a desired degree, the composition can be subjected to suitable conditions necessary for decomposing the gas producing, pore-forming agent to generate a residue and a gas. For a closed foam application, the pores are preferably disjoint and the composition will have trapped gas pores therein. Such composition do not need to be extracted. However, if the residue is extractable, then the residue can be extracted after formation. For application that require permeability, the gas can be allowed to escape forming interconnections between pores that eventually lead to a surface of the composition. These permeable composition are generally extracted to remove the residue.

Extract of composition having high concentration of disjoint pores is generally carried out in the presence of an extracting solvent and a solvent that swells the polymer matrix, but does not adversely affect the formation of void volumes as the pore-forming agent is leached from the disjoint pores. Swelling is thought to allow the leaching or extracting solvent or reagent to diffuse into the pores and dissolve or extract the pore-forming agent from the pores. Of course, if the resulting pore volumes are substantially larger than relative volume to the particle contained in the pores, then leaching can be skipped provided the composition is not meant to be used in applications that involve permeation of the composition by a material that could extract or react with the unleached pore-forming agents. Generally, the term substantially larger means that the resulting pore volume is at least 50% greater than the particle volume the generated the pore, preferably 100% greater, particularly 150% greater and especially 200% greater.

Polymers, Polymer Matrices and Polymer Compositions

Suitable polymers for use in this invention include, without limitation, any polymer material (homopolymers, copolymers, terpolymers or higher order multi-monomer polymers) or mixtures or combinations thereof into which one or more pore-forming agents can be introduced, dispersed, optionally force developed and later leached out of the composition leaving void spaces behind. Non-limiting examples of such polymers include polymers of any polymerizable monomer such polyolefin including polyalk-1-enes (polyethylene, polypropylene, copolymers of ethylene and propylene), vinyl aromatic polymers including polystyrenes, polysubstituted styrenes, polyvinyl pyridine, or the like, polyacrylates including polyacrylic acid, polymethacrylic acid, polymethacrylates, polyacrylated, polyesters such as PET, polylactides, and polyglycolides, polyurethanes, polymers containing one or more diene monomers including butadiene, isoprene, substituted butadienes or isoprenes, polyamides including polypeptides, polyimdes, polyacids, polyarylsulfides, polyarylsulfones, polycarbonates, EVAs, polyvinylacetates, polyvinylalcohols, polycaprolactones, polyanhydrides, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), poly(methyl vinyl ether), poly(maleic anhydride), chitin, chitosan, or non-carbon containing polymers such as polyphospoamides, or any other dissolvable or meltable polymer or copolymers, terpolymers, or higher poly-monomer polymers thereof or combinations or mixtures thereof.

Bio erodible polymers such as polyanhydrides or bulk erodible polymers such as polyorthoesters, including, without limitation, poly(l-lactic acid) (PlLA), poly(dl-lactic acid) (PLA), poly(glycolic acid) (PGA), polycaprolactones, copolymers, terpolymer, higher poly-monomer polymers thereof, or combinations or mixtures thereof are preferred biocompatible, biodegradable polymers. The preferred biodegradable copolymers are lactic acid and glycolic acid copolymers sometimes referred to as poly(dl-lactic-co-glycolic acid) (PLG). The co-monomer (lactide:glycolide) ratios of the PLG polymers are preferably between about 100:0 to about 50:50 lactic acid to glycolic acid. Most preferably, the co-monomer ratios are between about 85:15 and about 50:50 lactic acid to glycolic acid. Blends of PLA with PLG, preferably about 85:15 to about 50:50 PLG to PLA, are also used to prepare polymer materials. PLA, PlLA, PGA, PLG and combinations or mixtures or blends thereof are among the synthetic polymers approved for human clinical use. These copolymers offer the advantage of a large spectrum of degradation rates from a few days to years by simply varying the copolymer ratio of lactic acid to glycolic acid.

Suitable Solvents

Suitable polymers for use in the present invention can be used directly or with a suitable solvent to form polymeric solutions. The solubility or miscibility of a polymer or polymer blend in a particular solvent will vary according to factors such as crystallinity, hydrophilicity, hydrophobicity, capacity for hydrogen-bonding, ionic bonding capacity, molecular weight and molecular weight distribution. Consequently, the molecular weight and the concentration of the polymer in the solvent can be adjusted to achieve desired miscibility and/or viscosity.

In general, the polymers are dissolved in a suitable organic solvent. Of course, the solvent should not adversely affect the polymer or the particulated materials dispersed therein. The relative amount of solvent will have a minimal effect on the structure of the produced materials, but will affect the solvent evaporation time.

Suitable solvents include, without limitation, hydrocarbons solvents (saturated, unsaturated, cyclic, acyclic and/or aromatic) such as pentane, hexane, heptane, octane, nonane, decane, petroleum ethers or the like, hexenes, octenes, decenes or the like, cyclohexane, cyclohexene, cyclopentane, or the like, benzene, toluene, pyridine, pyrrole, or the like, mineral spirits, terpentine, or the like, halogenated solvents (fluorinated, chlorinated, brominated, iodated or mixed halogenated solvents) such as methylene chloride and bromide, freons, bromochloromethane, chloroform, carbontetrachloride, or the like, oxygenated solvents such as ketones, ethers, esters, carboxylic acids, aldehydes, alcohols, carbonates, or the like, nitrogen containing solvents such as amines, amides, or the like, sulfur containing hydrocarbon solvents such as sulfoxides, sulfonates, or the like, other hetero atom containing hydrocarbon solvents, mineral acids such as sulfonic acid, sulfuric acid, phosphoric acid, nitric acid, or the like or any other substance capable of dissolving the desired polymer or polymer mixture, or combinations or mixtures thereof.

Some preferred solvents include, without limitation, N-methyl-2-pyrrolidone, 2-pyrrolidone, C2 to C6 alkanols, propylene glycol, acetone, alkyl esters such as methyl acetate, ethyl acetate, ethyl lactate, alkyl ketones such as dimethylketone, diethylketone, and methyl ethyl ketone, dialkylamides such as dimethylformamide, dialkylsulfoxides such as decylmethylsulfoxide and dimethyl sulfoxide, dimethyl sulfone, cyclic ethers such as tetrahydrofuran, cyclic amides such as caprolactam, oleic acid, propylene carbonate, aromatic amides such as N,N-diethyl-m-toluamide, 1-dodecylazacycloheptan-2-one, and chlorinated solvents such as methylene chloride, chloroform or the like.

Pore-Forming Agent

Suitable pore-forming agents include any substance, combination or mixture of substances that are insoluble or substantially insoluble in the polymer composition or final polymer matrix (after solvent removal or after cooling) and can be removed from the polymer matrix leaving pores, voids or spaces in the matrix using any technique well-known in the art such as leaching with one or more leaching agents. Of course, the removal process should not significantly adversely affect the polymer matrix and should not significantly cause the polymer matrix to coalesce closing off or collapsing the volume occupied by the pore-forming agent or agents. Moreover, if vibratory agitation was used to disperse the particles in the polymer matrix, then the agitation will have caused the particles to create void spaces that are generally larger to much larger than the size of the particle being agitated. Depending on the direction, frequency and amplitude of vibratory agitation, the void space that will be left behind after particle extraction can be generally spherical or non-spherical, i.e., elongate.

Suitable pore-forming agents can include any substance, combination or mixture of substances that is insoluble or substantially insoluble in either the starting polymer composition (solution or melt) or in the final polymer matrix. Non-limiting examples of suitable pore-forming agents, include: mono, di, tri and polysaccharides including erythrose, arabinose, xylose, ribose, lyxose, glucose, mannose, gulose, idose, talose, altrose, allose, sorbose, tagotose, fructose, sucrose, lactose, maltose, meliboise, cellobiose, trehalose, raffmose, melitose, or the like; amino acids; solid hydrocarbons and hydrocarbons containing one or more hetero atoms including naphthylene, benzoic acid, stearic acid or the like; carboxylic acids salts such as alkali metal salts including halide salts (fluorides, chlorides, bromides and iodides), carbonate salts, carboxylic acid salts, perchlorate salts or the like, alkaline metal salts such as including halide salts (fluorides, chlorides, bromides and iodides), carbonate salts, carboxylic acid salts, perchlorate salts or the like, ammonium salts including halide salts (fluorides, chlorides, bromides and iodides), carbonate salts, carboxylic acid salts, perchlorate salts or the like, phosphonium salts including halide salts (fluorides, chlorides, bromides and iodides), carbonate salts, carboxylic acid salts, perchlorate salts or the like, polymers such as hydroxylpropylcellulose, carboxymethylcellulose, polyethylene glycol, polyvinylpyrrolidone, or the like.

All of the compounds listed above are included in this group as well as substances that can be decomposed by digestion in a leaching environment that will not in turn digest the polymer matrix. Thus, pore-forming agents that are digested or reacted away with strong acids or bases can be used provided that the digestion medium does not significantly adversely affect the integrity and variable porosity and/or permeability of the polymer matrix.

Besides the compounds noted above, suitable pore-forming agents include compounds that decompose upon heating, upon being subjected to strong electric or magnetic fields or compounds that can be selectively melted by sonic, microwave, infrared or other energy or compounds that can be decomposed by exposure to radiation or other ionizing energy sources. The only requirement for the pore-forming agents in any of the applications to which the compositions of the present invention can be used is that the substances must be insoluble or substantially insoluble in the starting polymer composition or in the final polymer matrix and extractable or otherwise removable from the final matrix without substantially adversely affecting the final matrix.

Suitable gas producing, pore-forming agents include, without limiation, carbonates, bicarbonate, carboxylic acids or derivatives thereof that for carbon dioxide upon heating, diazo-compound of the general formula (I):

$$R—N{=}{=}{=}N—R \qquad (I)$$

where the R group can be the same or different and can be any group allows the compound to thermally decompose to generate nitrogen gas. Other gas producing compounds can be used as well as are well known in the art as blowing agents.

One class of pore-forming agents are substances that are water soluble where their water solubility ranges from infinitely soluble to soluble with very soluble being preferred. It should be recognized that any degree of water solubility will permit leaching; however, the time required will be inversely proportional to the solubility of the agent in water. This class of agents is generally used for polymers and polymer mixtures that are soluble in organic solvent and insoluble or substantially insoluble in water or aqueous environments. Another class of pore-forming agents are lower alcohol soluble agents. This class is preferred for those polymer and polymer mixtures that are insoluble in lower alcohols.

For water soluble polymers, the preferred class of pore-forming agents should be water insoluble or substantially water insoluble agents. Such water insoluble organic reagents includes, without limitations, ketones, aldehydes, alkenes, alkanes, cyclic hydrocarbons, aromatic hydrocarbons such as naphthalene and higher polycyclic aromatic hydrocarbon, halogenated hydrocarbons, or the like.

Again, the only requirement for any pore-forming agent is that the agent must not have appreciable solubility (preferably little to no solubility) in the polymer matrix or its precursor solution or melt and must be soluble (preferably very soluble) in a solvent in which the polymer matrix does not have appreciable solubility (preferably little to no solubility). However, the solvent can cause the polymer matrix to swell as long as the matrix does not substantially or significantly rearrange during the leaching process to either collapse forming pores or melt pores together.

The matrix is not considered to be significantly rearranged, if the pore-forming agents are removed with less than 35% loss in pore volume, i.e., no more than 35% of volume originally occupied and/or formed by pore-forming agent(s) is lost during leaching assuming 100% leaching efficiency. The 35% target should be reduced appropriately for less than complete leaching efficiency. Thus, if leaching efficiency is only 85%, then not significantly rearranged means that no more than 35% of the 85% pore volume is loss during leaching. The matrix is not considered to be substantially rearranged, if the pore-forming agents are removed with less tafn 15% loss in potential pore volume. Preferably, the rearrange or loss in potential pore volume due to leaching should be less than 10% and particularly less than 5%.

The concentration of pore-forming agent relative to polymer in the composition will vary according to the degree of pore-formation desired. Generally, this concentration will range from about 0.01 g to about 200 g of pore-forming agent per gram of polymer. Preferably, this concentration will range from about 10 g to about 150 g of pore-forming agent per gram of polymer. More particularly, this concentration will range from about 50 g to about 150 g of pore-forming agent per gram of polymer. Most particularly, this concentration will range from about 50 g to about 125 g of pore-forming agent per gram of polymer. And, most preferably, this concentration should be at least 50 g of pore-forming agent to polymer with the upper limit being the point at which not more agent can be incorporated into the polymer matrix.

For biological applications, suitable pore-forming agent are preferably biocompatible, soluble in body fluids or capable of being biodegraded or bio assimilated in the body and relatively non-toxic.

Particle Leaching

The resulting polymeric matrix with the solid particles distributed variably therein is then leached to remove the dispersed solid particles. The leaching step is generally accomplished by immersing the matrix in a leach agent which is preferably a liquid in which the particles are soluble. Leaching is continued for a sufficient amount of time to allow leaching of substantially all of the particles, but which does not dissolve or detrimentally alter the polymer matrix.

For compositions composed of water insoluble or substantially water insoluble polymers or polymer mixtures, the preferred leaching agent is water, most preferably distilled-deionized water, which does not dissolve the polymer nor cause measurable hydrolysis of the polymer within the time required for processing. Preferably, the particle is leached out of the material in a vessel containing distilled-deionized water for a period of forty-eight hours with the water being changed approximately every twelve hours. The vessel can be placed in a heated water bath or incubator and shaken to enhance particle leaching. Most preferably, the vessel of water is placed in a water bath heated to approximately 37° C. and can be shaken at approximately 100 rpm to enhance the leaching process.

For organic insoluble or substantially organic insoluble polymers, organic solvents such as alcohols, aromatic solvents, aliphatic hydrocarbon solvents, ketones, halogenated solvents or similar solvents can be used provided that the leaching solvent does not adversely affect the polymeric matrix.

Permeability of the Polymer Matrix

Removal of the particles creates a polymer material having a plurality of pores, spaces or voids in the material formerly occupied by the particles. Of course, these pores, spaces or voids can be either isotropically or anisotropically distributed throughout the matrix so that the matrix has substantially uniform, differential or variable permeation to components of complex fluid mixtures such as blood or other bodily fluids, reaction mixtures, pharmaceutical mixtures, extraction mixtures, hazardous waste mixtures, or other mixture of components.

In fact, the composition can have region where the permeation or migration propensity of the composition to a given range of materials is very low to zero (i.e., less than about 20%, preferably less than about 10%, particularly less than about 5% and especially less than 1% with 0% being an ultimate goal) or very high (i.e., greater than about 50%, preferably greater than about 70%, particularly greater than about 80% and especially greater than 90% and 100% being an ultimate goal).

Such permeation can be measured either as to a particular component or using its hydraulic permeability given by the formula (Darchy's law) of equation (1)

$$K = \frac{h \Delta V}{A \Delta P \Delta t}$$

where K is the permeability, h is the height of the object being tested, $\Delta V$ is the volume change in the solution in contact with the object, A is the surface area of the object, $\Delta P$ is the pressure differential, and $\Delta t$ is the time. Darchy's law is designed to measure the permeation of a material to water, but the same principal can be used to define a permeability for other solvents or for constituents in a solution.

In the case of the composition of the present invention that have permeabilities measured by their hydraulic permeability, the permeable part(s) of the compositions should have a hydraulic permeability K greater than or equal to about $1 \times 10^{-11}$, preferably greater than or equal to about $1 \times 10^{-9}$, particularly greater than or equal to about $1 \times 10^{-7}$ and especially greater than or equal to about $1 \times 10^{-5}$. Alternatively, the impermeable part(s) of the implants of the present invention should have a hydraulic permeability less than about $1 \times 10^{-13}$, preferably less than or equal to about $1 \times 10^{-15}$, particularly less than or equal to about $1 \times 10^{-17}$ and especially less than about $1 \times 10^{-19}$.

Moreover, to attain a permeability sufficient to allow macromolecular and cellular components of bodily fluids to permeate the implant, the implant or region thereof should have at least 20% of the pores in an interconnected state, preferably at least 30% of the pores in an interconnected state, particularly at least 40% of the pores in an interconnected state and especially at least 50% of the pores in an interconnected state. By interconnected state, the inventors mean that the pores are connected in such a way as to allow a give class of material to migrate from one pore into an interconnected cell. Generally, permeability increases when the number of interconnected pores increases.

Porosity of the Polymer Matrices

The size and/or quantity of a pore-forming agent incorporate in the polymer matrix, the distribution of the pore-forming agent within the polymer matrix, the frequency, direction and magnitude of agitation, among other factors, influence pore size and porosity of the polymer matrix. Where the implant is employed for the purpose of tissue regeneration, as for example, to promote guided tissue regeneration of periodontal tissue, it is preferred that the diameter of the pores in the matrix be effective to deter growth of epithelial cells into the polymer matrix of the implant, and enhance growth of connective tissue cells into the matrix.

Porosity is generally measured by the formula equation (2):

$$Porosity = \frac{V_v}{V_t} * 100 \qquad (2)$$

where $V_v$ is the void volume and $V_t$ is the total volume.

Preferably, the size of the pores and porosity of the matrix of the implant are distributed and interconnected to an extent sufficient to facilitate the diffusion of nutrients and other growth-promoting substances such as growth factors, to cells which have grown into the matrix. Of course, for those regions of the implants where diffusion is not desired, then the porosity should be relatively low or the pores should be disjoint. That is, the implant could have a high porosity and yet have low permeability to bodily fluid including water or the implant could have low porosity and in turn low permeability to bodily fluids.

Generally, the pores in the implants can range in diameter from about 1 μ to about 1000 μ. However, larger and smaller pores can also be formed in the matrix using larger or smaller particulate materials. Preferably, the pores size ranges from about 50 to about 500 microns, more preferably between about 50 to about 400 microns, and most preferably between about 75 to about 300 microns. Of course, the implants of the present invention can have pores size distributions that are mono-modal, bi-modal or polymodal depending on the number of different pore-forming agents used and their particle size distributions and on agitation amplitude, direction and frequency.

It is further preferred that the degree of porosity of the matrix is such that the matrix is capable of substantially maintaining structural integrity for a desired period of time without breakage or fracturing. Of course, if the article is designed to degrade with time, then its porosity and permeability characteristics will also change as degradation proceeds. The time for degradation can be controlled by the judicious choices of pore-forming agents and polymers and by the specific processing steps used to prepare the matrix.

The size or diameter of the pores formed in the matrix may be modified by the size and/or distribution of the pore-forming agent within the polymer matrix. For example, pore-forming agents which are relatively insoluble in the polymer mixture, may be selectively included in the composition according to particle size to generate pores having a diameter which corresponds to the size of the pore-forming agent. Pore-forming agents which are soluble in the polymer mixture can also be used and may vary the pore size and porosity of the polymer matrix according to the pattern of distribution and/or aggregation within the mixture and resulting polymer matrix.

The size or diameter of the pores formed in the matrix may be modified by the size and/or distribution of the pore-forming agent within the polymer matrix. For example, pore-forming agents which are relatively insoluble in the polymer mixture, may be selectively included in the composition according to particle size to generate pores having a diameter which corresponds to the size of the pore-forming agent. Pore-forming agents which are soluble in the polymer mixture may vary the pore size and porosity of the polymer matrix according to the pattern of distribution and/or aggregation within the mixture and resulting polymer matrix. Again, the amplitude, direction and frequency of agitation will also affect the size and shape of the pores formed by the particles, especially rigid particles and particles insoluble in the polymer matrix.

The articles made from the compositions of the present invention can have porosities that range from about 0% and about 99%, depending on what region of the article is being measure. For highly porous regions, porosities are preferably between about 50 and about 99%, and particularly between about 75% and 99%. Of course, the porosity could vary from substantially 0% to 99% over any given profile of the article. Pore diameter and distribution within the polymer matrix may be measured, as for example, according to scanning electron microscopy methods by examination of cross-sections of the polymer matrix. Porosity of the polymer matrix may be measured according to any suitable method, as for example, mercury intrusion porosimetry, specific gravity or density comparisons, calculation from scanning electronic microscopy photographs, and the like. Additionally, porosity may be calculated according to the proportion or percent of water-soluble material included in the polymer composition. For example, a composition which contain about 30% polymer and about 70% pore-forming agents before leaching ideally will generate a polymer matrix having a porosity of about 70%.

Of course, because the present implants have variable permeability and/or porosity, the exact permeation and/or porosity of a given part or portion of the composition or object made therefrom can be tuned from substantially impermeable and/or non-porous to highly to completely permeable and/or porous to a given material or class of materials.

Incorporation of Other Materials

The compositions may further contain other materials such as fillers to improve the strength of the polymer matrices, materials that will aid in degradation, antidegradants such as anti-oxidants and anti-ozonants, biologically-active agent, colorants, chromophores or light activated (fluorescent or phophorescent) tags or any other material that may alter or change the property of the compositions.

Referring now to FIG. 1, an object such as an implant or a membrane of an embodiment of the compositions of the present invention, generally 10, can be see to comprise a polymer matrix 12 having dispersed therein pores 14. The pores 14 can be seen to increase in frequency from a top 16 of the object 10 to a bottom 18 of the object 10.

If the object is an implant, then the implant could be oriented in site of injuring or surgical removal either with the top 16 in contact with the injuring site or with the bottom 18 in contact with the injuring site. If the orientation is the latter, then blood flow will be restricted from the injury site into surrounding tissue, yet the site of injury would be able to repair and regenerate using the enhanced permeability and/or porosity of a lower region 20 of the object 10.

It should be recognized that the permeability and/or porosity of the object varying from its lower region 20 to its upper region 22. This variation is the result of an applied force acting on pore-forming agents during the preparation of the composition out of which the object 10 was formed. It should also be recognized that as a density or frequency of pores increases, the pores may not represent a single void as shown in FIG. 1, but adjacent pores may have points and/or areas of contact. When individual pores have points or areas of contact, then the volume of the resulting void area is the sum of the interconnected pores. Such interconnections can yield macro-voids and even regular or irregular channel-like structures in the matrix.

Preferably, as shown in FIG. 1, the top 16 of the object 10 is pore free or impermeable. Of course, the upper region 22 could also simply be less porosity (fewer pores) than the lower region 20. Moreover, the composition can be such that the biodegradability (the rate at which biodegradation occurs) could also be different for the upper region 22 and the lower region 22. This result can be achieved by using two different polymers having different densities in the preparation of the composition so that gravity or whatever other applied force is used to induce a variation in particles density in the matrix can also induce a variation in the composition of the matrix due to differential sedimentation of the different polymers used to make the compositions.

Figure 2:
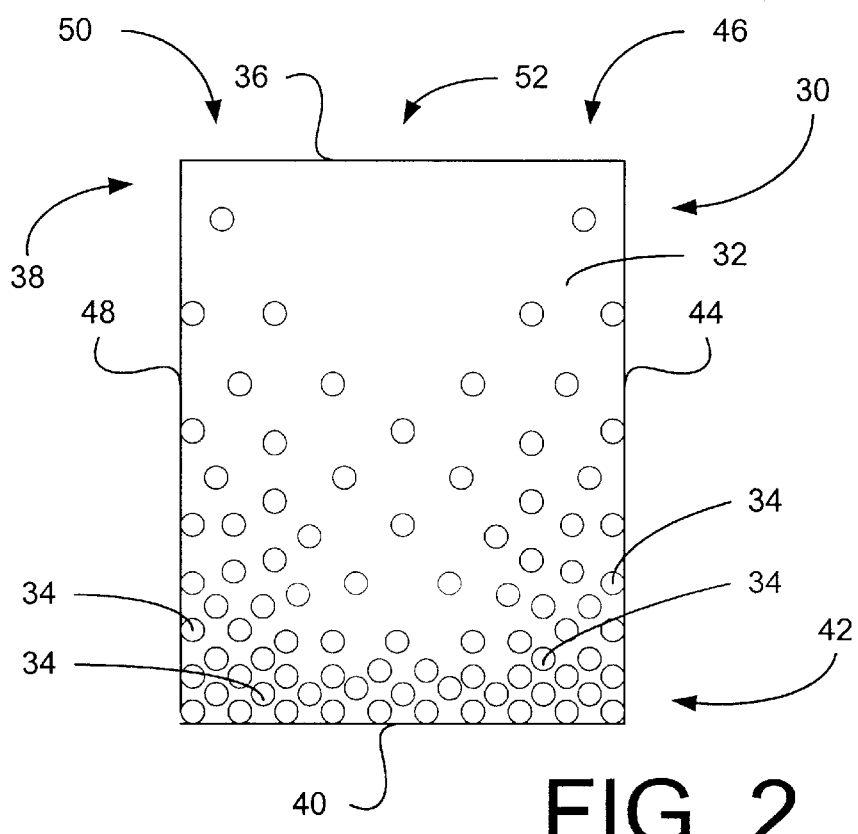
FIG. 2 is a cross-sectional view of a second embodiment of an object prepared from a composition of the present invention having a double force induced variation in permeability and/or porosity.

Referring next to FIG. 2, another embodiment of an object made from the compositions of the present invention, generally 30, can be see to comprise a polymer matrix 32 having dispersed therein pores 34. The object 30 further includes a top 36, an upper region 38, a bottom 40, a lower region 42, a right side 44, a right region 46, a left side 48 and a left hand region 50. Unlike the object 10 of FIG. 1, the object 30 is the result of a preparation of a composition of the present invention in which two applied forces were used to induce a two dimensional variable distribution of pores in the matrix. Thus, the pores density not only variation from top to bottom, but also from left to right. It should be recognized that the composition from which the object 30 was prepared used a static force like gravity and a radial force like centripetal force to induce the two dimensional variation in pore density. Again, the object 30 has a substantially impervious or impermeable top or less permeable upper region and a less permeable (fewer pores) central region 52. Again, this composition can also be made with different polymers so that the resulting composition will not only have a two dimension variation in pore density, but also a two dimensional variation in composition.

Figure 3A:
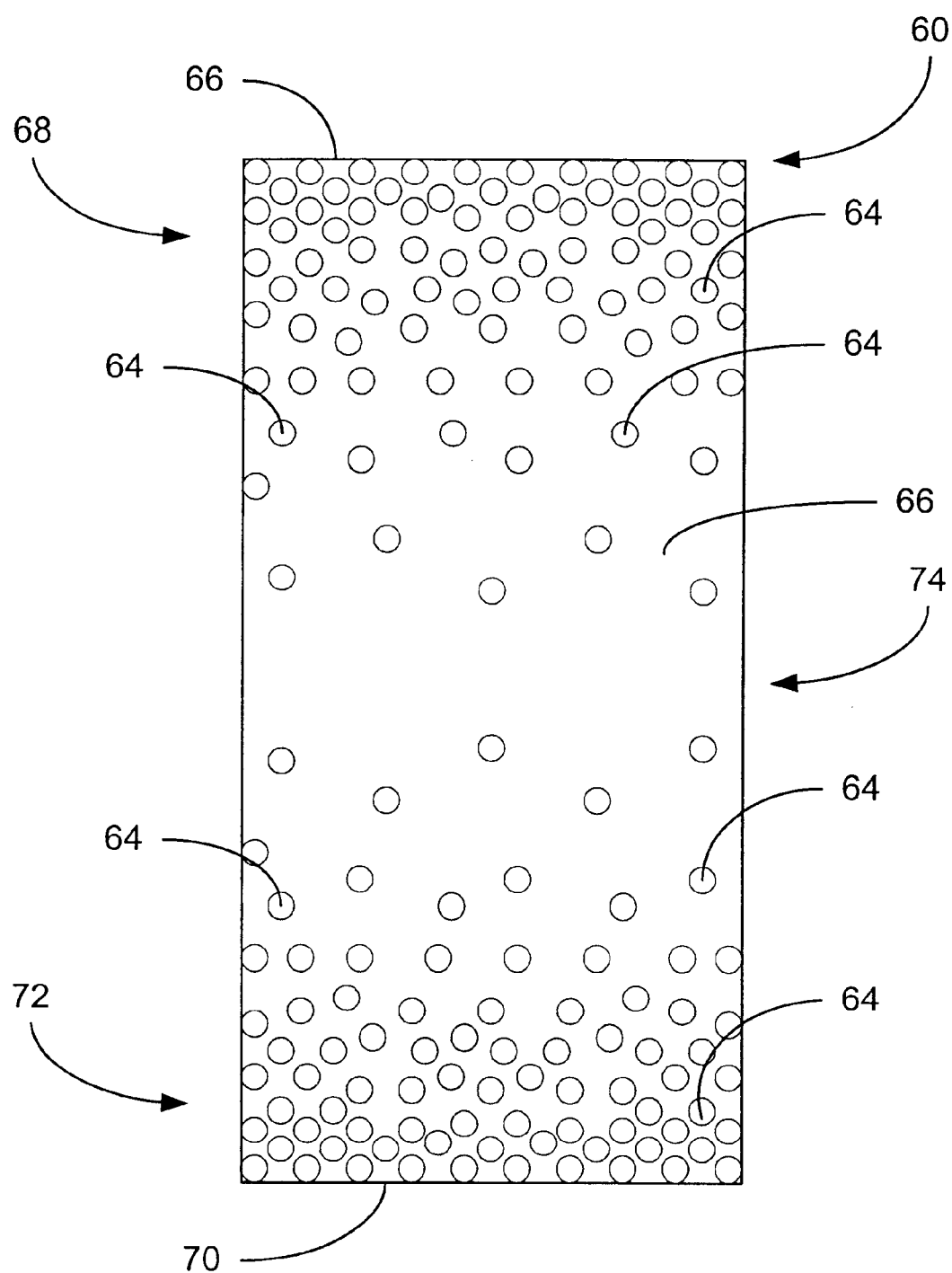
FIG. 3a is a cross-sectional view of a third embodiment of an object prepared from a composition of the present invention having a single force induced variation in permeability and/or porosity with respect to two different pore-forming agents.

Looking now to FIG. 3a, yet another embodiment of an object made from the compositions of the present invention, generally 60, can be see to comprise a polymer matrix 62 having dispersed therein pores 64. The object 30 further includes a top 66, an upper region 68, a bottom 70, a lower region 72 and a central region 74. The object 60 derives from a composition in which two different pore frowning agents were used. One pore frowning agent had a density greater than the matrix density and the other had a density less than the matrix density. During gravity development or development by another static force; the heavier particles settled towards the bottom 70 of the object 60, while the lighter particles rose toward the top 66 of the object 60. Thus, the upper region 68 and the lower region 72 have similar porosities and/or permeability, while the central region 72.

Figure 3B:
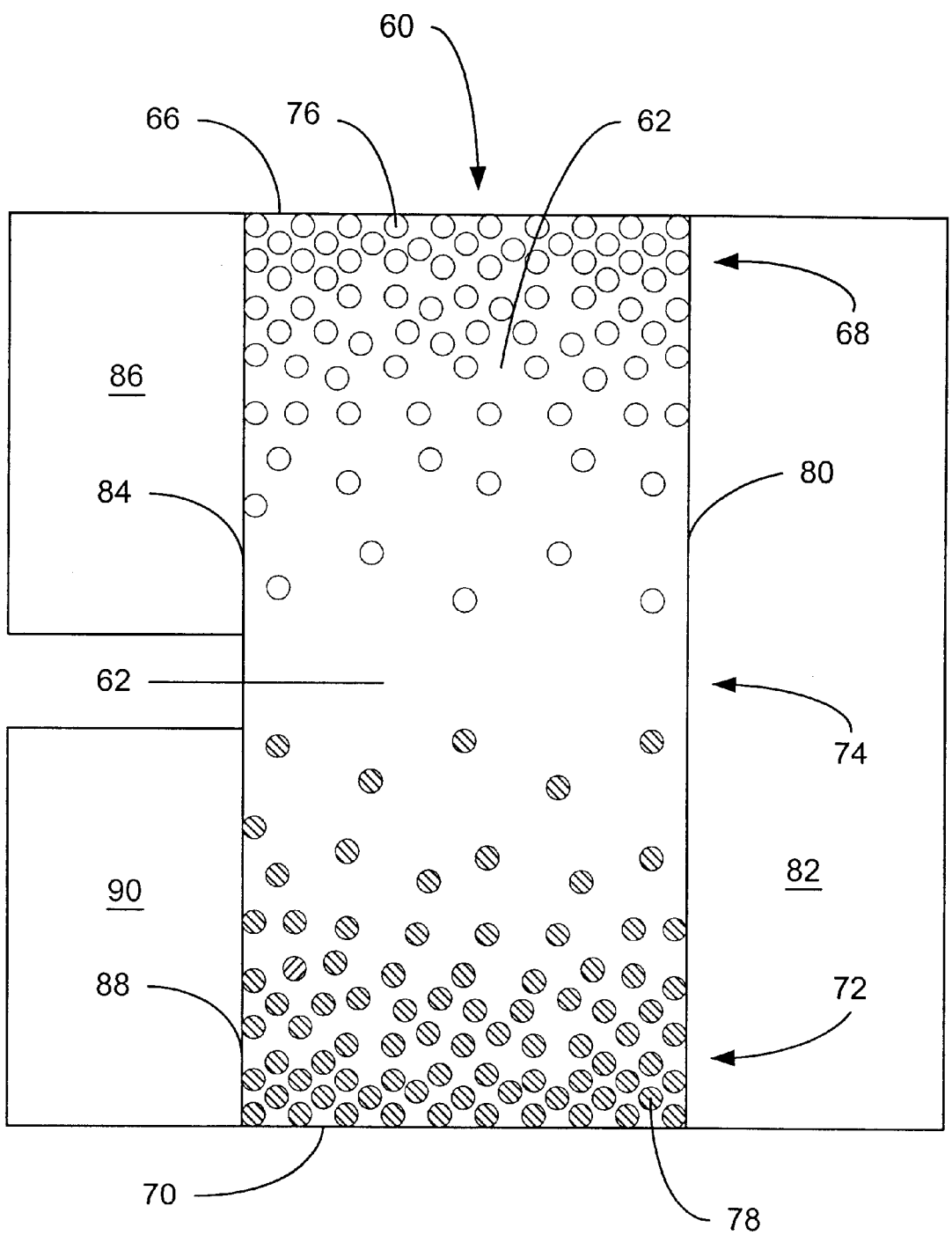
FIG. 3b is a cross-sectional view of the object of FIG. 3a as it may be used to channel components from one vessel into other vessels.

Referring now to FIG. 3b, the object 60 of FIG. 3a can be seen to have two sizes of pores. A first pore size associated with upper pores 76 (pores concentrated in the upper region 68) and a second pore size associated with lower pores 78 (pores concentrated in the lower region 72). The object 60 of FIG. 3b also includes the central region 72 which is substantially or completely devoid of pores. Thus, the object 60 is now a differential permeable membrane capable of channeling different materials to different output zones.

As can be seen in FIG. 3b, a right hand side SO of the object 60 is placed in fluid contact with an input vessel 82 containing a solution of different sized components and an upper left side portion 84 is placed in fluid contact with a first output vessel 86 and a lower left side portion 88 is placed in fluid contact with a second output vessel 90. Because the upper and lower pore sizes are different, the upper region 68 will permit permeation of components having a size less than an upper region permeation size and the lower region 72 will permit permeation of components having a size less than a lower region permeation size. Thus, the components in the input vessel 82 which are less than the upper region permeation size will migrate or diffuse through the upper region 68 of the object 60 into output vessel 86. The components in the input vessel 82 which are less than the lower region permeation size will migrate or diffuse through the lower region 72 of the object 60 into output vessel 90. And, the components in the input vessel 82 which are larger than the upper and lower permeation sized will remain in the input vessel 82. This type of composite object of the present invention can be used in selective filtration or in semi-permeable membrane application as well as in implant and tissue carrier application where it can be used to direct different classes of bodily components to different areas of a tissue site in contact with the implant. Thus, the composite could be designed to present any fluid flow to occur through a given surface or region of the composite and at the same time to direct cellular components somewhere else and enzymes to other areas only.

Figure 4:
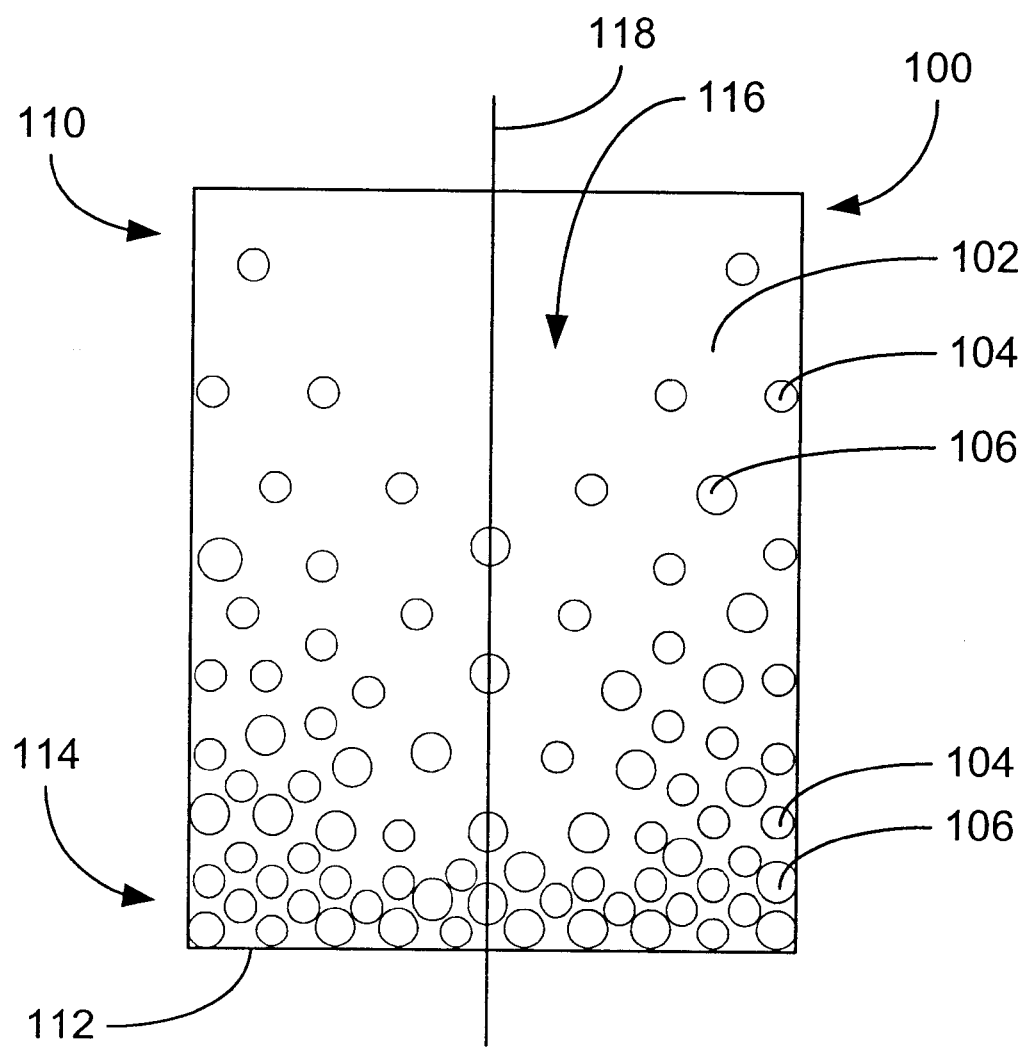
FIG. 4 is a cross-sectional view of another embodiment of an object prepared from a composition of the present invention having a double force induced variation in permeability and/or porosity using two different sized pore-forming agents.

Referring now to FIG. 4, yet another embodiment of an object made from a composition of the present invention, generally 100, can be see to comprise a polymer matrix 102 having dispersed therein a first type of pore 104 having a first size and a second type of pore 106 having a second pore size. The object 100 further includes a top 108, an upper region 110, a bottom 112, a lower region 114 and a central region 116. The object 100 derives from a composition in which two different sizes of a given pore forming agent was used. The composition has made using two forces acting along mutually perpendicular axis, i.e., gravity acting up and down coupled with spinning about a central axis 118 of the object. Of course, the two forces do not have to act in a perpendicular arrangement for it is possible to spin the composition along any axis so that the angle between the centripetal and gravitional force vectors can be substantially zero degrees (parallel) or substantially 180° (perpendicular). Such an orientation can be easily accomplished by attached the machinery that spins and agitates the composition as it is being prepared and force developed on a platform that can be rotated through 180°.

Figure 5:
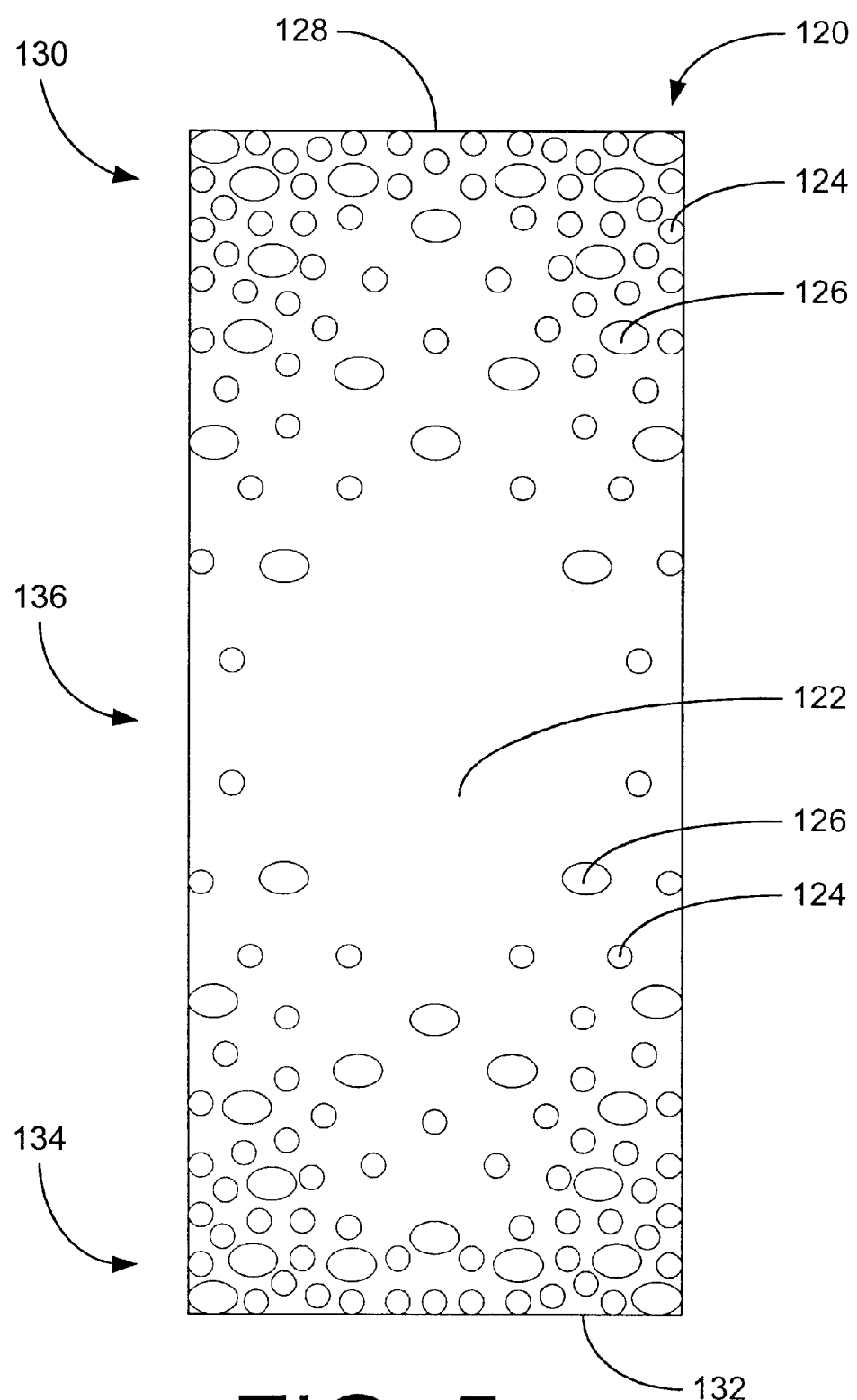
FIG. 5 is a cross-sectional view of another embodiment of an object prepared from a composition of the present invention having a double force induced variation in permeability and/or porosity using two different sized and shaped pore-forming agents.

Referring now to FIG. 5, yet another embodiment of an object made from a composition of the present invention, generally 120, can be see to comprise a polymer matrix 122 having dispersed therein a first type of pore 124 having a first size and shape and a second type of pore 126 having a second size and shape. The object 120 further includes a top 128, an upper region 130, a bottom 132, a lower region 134 and a central region 136.

The object 120 derives from a composition in which two different pore-forming agents were used; one having a density greater than the matrix and one having a density less than the matrix. Each pore-forming agent included particles of different sizes and shapes, shown here as two identical sizes and shapes, but one of skill in the art would recognize that any mixture of pore-forming agents of different sizes, shapes and densities can be used. The composition was developed using two different forces acting at right angles to each other; gravity acting from top to bottom and centripetal force acting from a central axis of the mold containing the composition to its sides.

It should be recognized that size and shape of the particles may affect the time it takes for force developed variations in the distribution of particles and/or different density polymers in the compositions. Thus, smooth and symmetric particles will generally move through the matrix at a faster rate under a developing force than will irregular, rough particles.

Moreover, larger particles will generally force develop faster than smaller particles provided the particles have similar smoothness and shape characteristics. The duration of application of the developing force will also depend on the viscosity of the matrix which in turn will depend on solvent, if any, concentration and temperature. Thus, raising the temperature of the composition will decrease development time.

Figure 6:
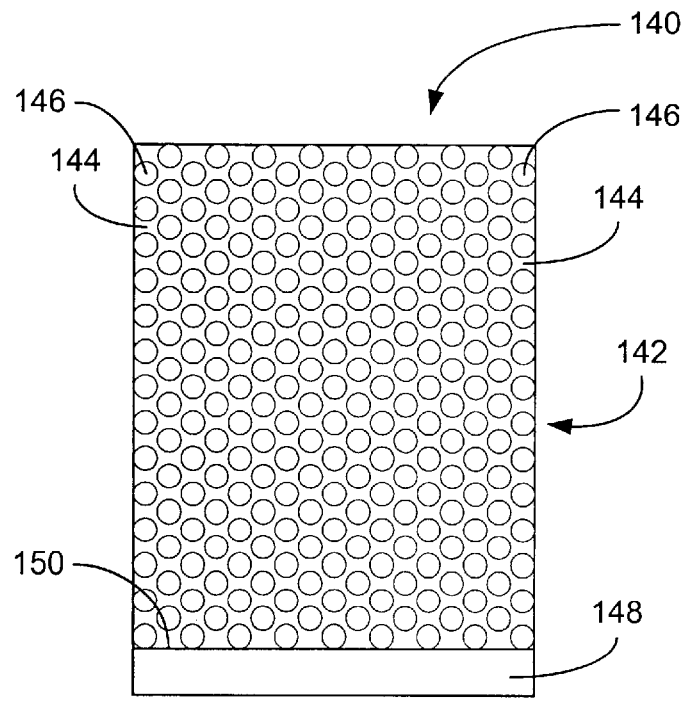
FIG. 6 is a cross-sectional view of a preferred embodiment of a composite object of the present invention prepared from a highly porous and/or permeable composition having associated with one surface an impermeable or non-porous layer.
Figure 7:
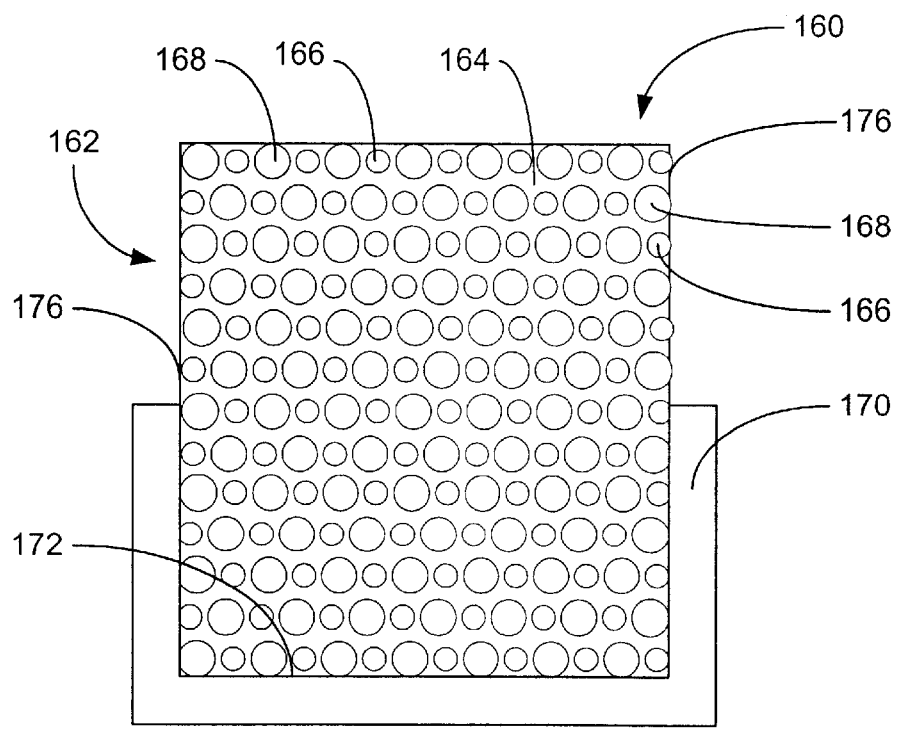
FIG. 7 is a cross-sectional view of another preferred embodiment of a composite object of the present invention prepared from a highly porous and/or permeable composition having different pores sizes and having associated with certain surfaces thereof an impermeable or non-porous layer.

Looking next at FIGS. 6 and 7, two composite structures of the present invention generally 140 and 160. The composite 140 includes a top part 142 composed of a polymer matrix 144 having dispersed therein pores 146. Preferably, the pores 146 are dispersed uniformly throughout the matrix 144 as shown in the figure. It should be recognized that although the pores 146 are shown as circles of a given diameter, in actuality the pores will be of a given range of particle sizes and shapes depending on the nature of the particles used and the particles size distribution of the particles used.

The composite 140 further includes a bottom part or layer 148 composed of a different material which is either impervious or impermeable or has a different permeability than the permeability of the top part 142. This composite structure can be prepared by coating a uniformly permeable material or composition made any procedure known in the art or by coating a composition of the present invention with a material having a different permeability and/or porosity. Preferably, the bottom layer 148 is substantially impervious, non-porous or impermeable so that the final composited will be impermeable on one surface and permeable on other surfaces. Of course, the bottom layer 148 could extend over only a portion of a bottom 150 of the top part 142.

The composite 160 includes a top part 162 composed of a polymer matrix 164 having dispersed therein a first set of pores 166 and a second set of pores 168. Preferably, the pores 166 and 168 are dispersed uniformly throughout the matrix 164 as shown in the figure. It should be recognized that although the pores 166 and 168 are shown as circles of a given diameter, in actuality the pores will be of a given range of particle sizes and shapes depending on the nature of the particles used and the particles size distribution of the particles used.

The composite 160 further includes a part or layer 170 composed of a different material which is either impervious or impermeable or has a different permeability than the permeability of the top part 162. The layer 170 extends over a bottom 172 of the top part 162 and up onto a portion 174 of side surfaces 176 of the top part 162. Of course, if the composite 160 is cylindrical in shape, then the side surfaces 176 is actually only as single surface.

Again, this composite structure can be prepared by coating a uniformly permeable material or composition made any procedure known in the art or by coating a composition of the present invention with a material having a different permeability and/or porosity. Preferably, the layer 170 is substantially impervious, non-porous or impermeable so that the final composited will be impermeable on one surface and permeable on other surfaces.

Figure 8:
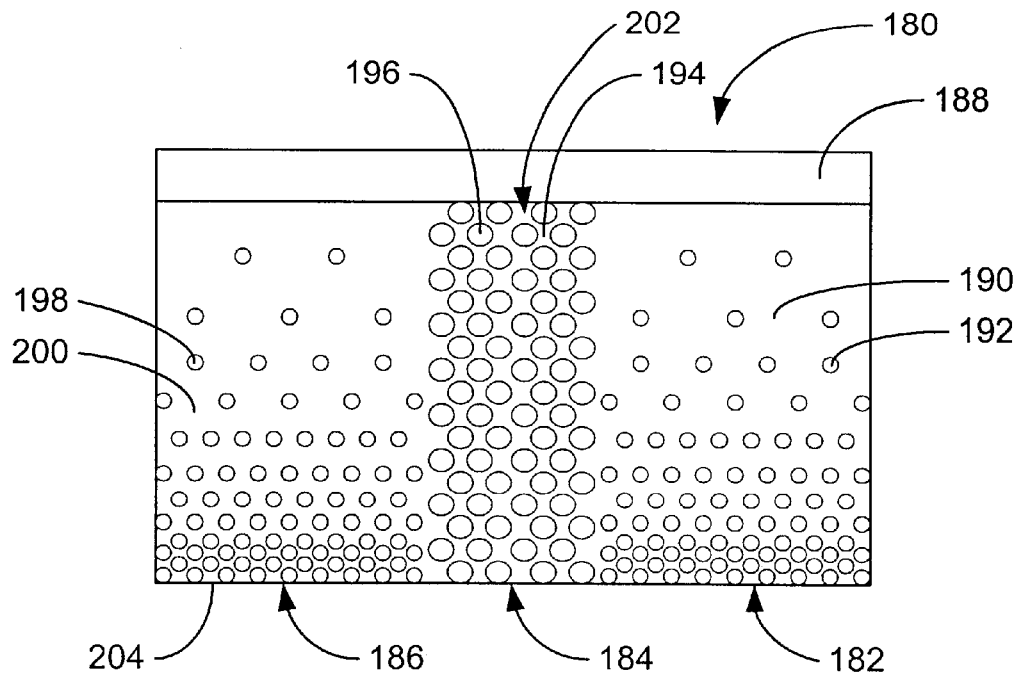
FIG. 8 is a cross-sectional view of another preferred embodiment of a composite object of the present invention prepared from a highly porous and/or permeable composition sandwiched between two single force induced variational permeable and/or porous compositions of the present invention having associated with one surface thereof an impermeable or non-porous layer.
Figure 9:
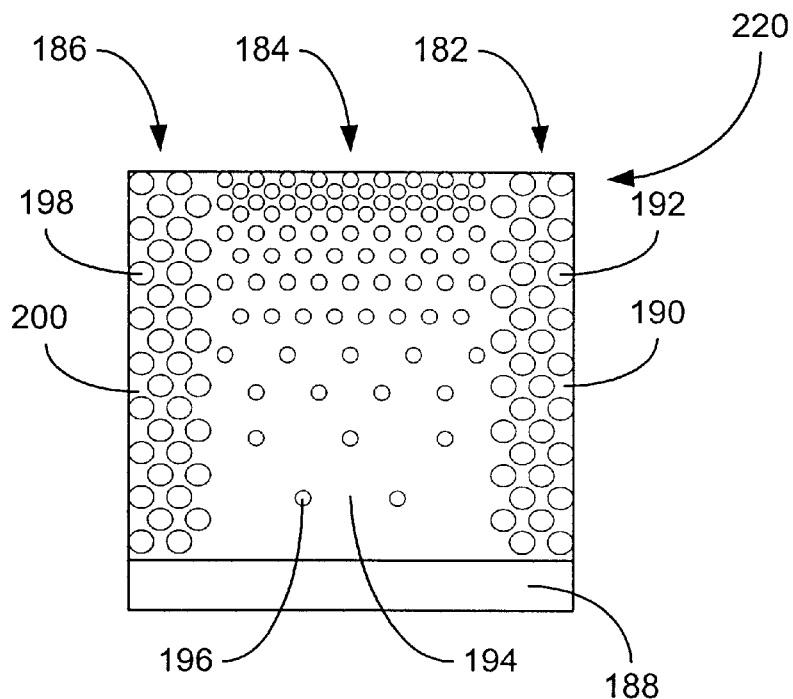
FIG. 9 is a cross-sectional view of another preferred embodiment of a composite object of the present invention prepared from a single force induced variational permeable and/or porous compositions of the present invention sandwiched between two highly porous and/or permeable composition and having associated with one surface thereof an impermeable or non-porous layer.

Referring now to FIGS. 8 and 9, two more complex composites of the present invention are shown generally as 180 and 220. The composite 180 includes a first component 182, a second component 184, a third component 186 and an optional forth component 188. These components can be adhesively bonded together or integrally fused to each other where integrally fused means that an exchange of material across the interface has occurred or one material can simply be coated onto another material. Thus, the optional forth component 188 could simply represent a coating or layer over surfaces of other components. The component 182 includes a polymer matrix 190 having dispersed therein pores 192. The component 184 includes a polymer matrix 194 having dispersed therein pores 196. And, the component 186 includes a polymer matrix 198 having dispersed therein pores 200. The components 182 and 186 are components having variable permeability and/or porosity that have been developed using a single applied force such as gravity. While component 184 has uniform porosity and/or permeability. Thus, by sandwiching component 184 between components 182 and 186, the composite 180 has an more porous interior region 202 do that the interior region 202 will allow the diffusion of larger species quickly into this area with diffusion into adjacent areas varying with the distance from a bottom 204 of the composite 180.

Alternatively, as shown in FIG. 9, the components 182 and 186 are now compositions that have a uniform permeability and/or porosity and the component 184 interposed therebetween having a variable permeability and/or porosity composition of the present invention. The composite 220 can also include a substantially impervious, non-porous and/or impermeable layer 188 deposited on a portion or an entire surface or as in FIG. 7, the layer 188 can be deposited over portion or one or more surface of the composite. Looking at FIGS. 6–9, it should be clear that many different composite structures and membranes can be constructed to facilitate channeling of molecular (biological or non-biological) species through different parts of the composite to either act as a selective filter, selective membrane or to selectively direct certain biological agents to one tissue site and other to other tissue sites. Thus, composites could be designed to direct growth factors to all tissues in contact with permeable areas of a composite, while directing antibiotics to one tissue site and not other tissue sites.

Figure 10:
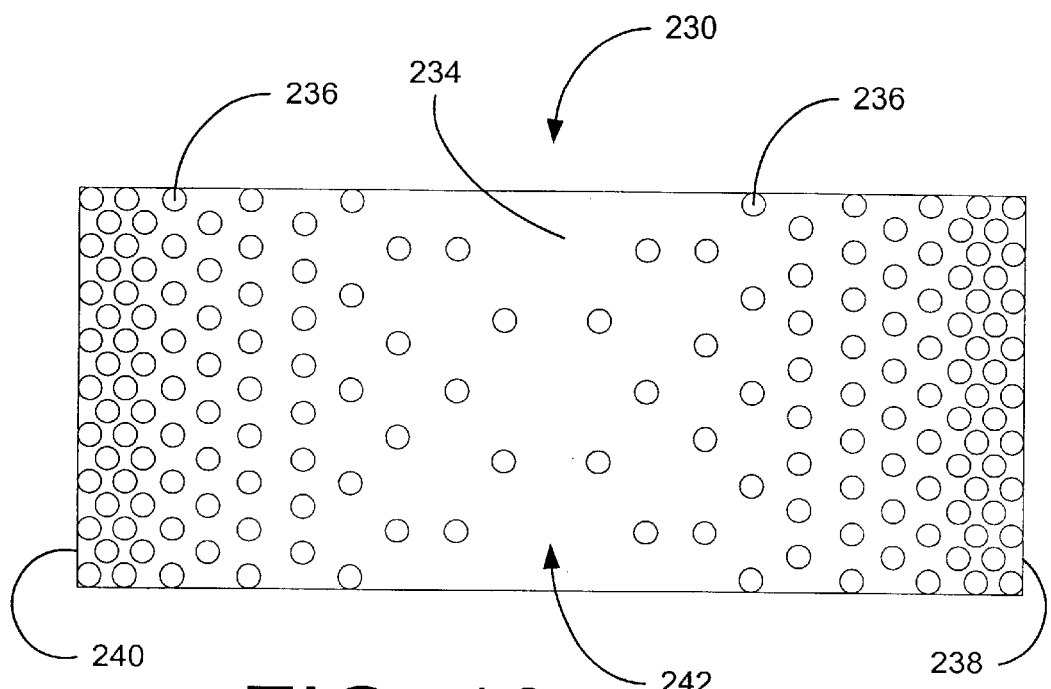
FIG. 10 is a cross-sectional view of a preferred embodiment of a membrane of the present invention prepared from a single force induced variational permeable and/or porous compositions of the present invention.
Figure 11:
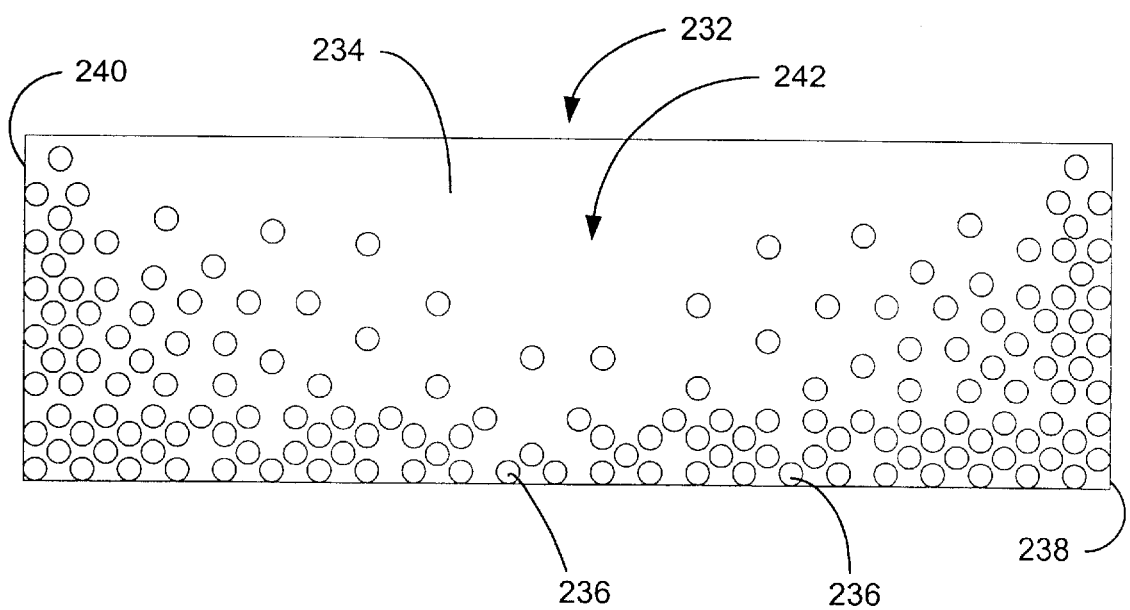
FIG. 11 is a cross-sectional view of another preferred embodiment of a membrane of the present invention prepared from a double force induced variational permeable and/or porous compositions of the present invention.

Referring now to FIGS. 10 and 11, membranes 230 and 232 are shown to comprise a polymer matrix 234 and pores 236. In membrane 230, the pores 236 are distributed in the matrix 234 in a sinusoidal distribution, i.e., highly concentrated in at ends 238 and 240 and substantially zero concentration in a center region 242. The membrane 230 can be prepared using centripetal force to induce the sinusoidal distribution shown in FIG. 10. If the mold is cylindrical, then membrane 230 could be circular or any part of a circle. If the mold is polygonal, then the membrane 230 could be polygonal shaped or any part thereof. Of course, by cutting out different parts of a centripetally developed composition of the present invention, the variation in porosity and/or permeability can be tailored to any particular use.

The membrane 232 is similar to the membrane 230 except that the composition was allowed to develop by the action of two forces, preferably centripetal and gravity working in conjunction. Again, the membrane 232 can be formed of any part of a two dimensionally developed composition as described above for membrane 230. It should also be recognized that the compositions of the present invention can be developed in more complex ways than by using only two forces. The composition could first be gravity developed, then centripetally developed along on axis and then along another axis. Moreover, if some of the pore forming agents are electrically active (charged ion pairs), then electrical developing can be performed on the electrically active agents after gravity and/or centripetal developing have been performed. This same procedure could be used for magnetically active agents (agent that will move when subjected to an external magnetic field). Again, it must be emphasized that electrically and magnetically mobile pore-forming agents must be capable of being leached from the matrix after development. In the case of ion pairs, generally water leaching will remove these species. In the case of magnetically active agents, if the agents can be leached by acid, base or chelating solutions that do not significantly decompose the polymer matrix, then the agents can be used in the present invention to make composition having variable permeability and/or porosity.

Figure 12:
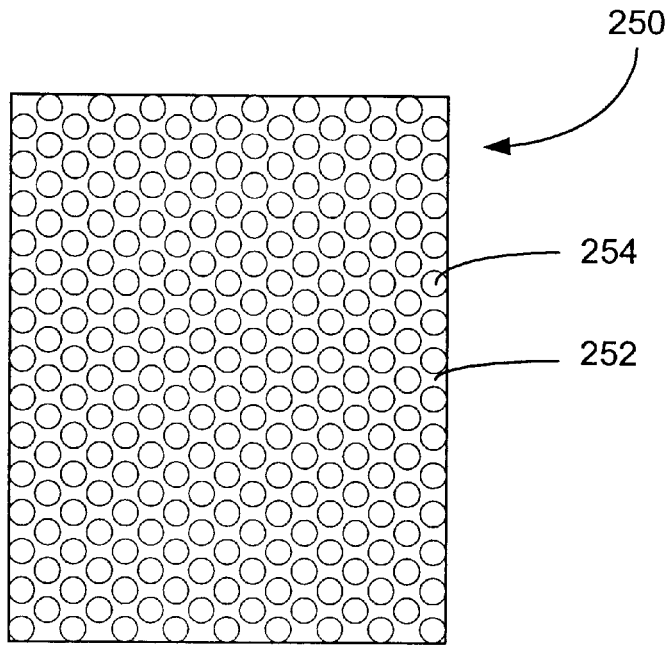
FIG. 12 is a cross-sectional view of a first embodiment of a substantially uniform, highly permeable and/or porous composition of the present invention.

Referring now to FIG. 12, a first embodiment of an object made from the compositions of the present invention, generally 250, can be seen to include a polymer matrix 252 and pores 254. It should be recognized that although the pores 254 are shown a geometrically and uniform circles, in reality the pores 254 will be a uniform size and shape without some limit depending on the type of pore-forming agent used to make the compositions of this invention. Thus, if the particles are substantially spherical and of a given particle size distribution, then the object will have uniform distribution of the spherical particles distributed throughout in accordance with the particle size distribution. If more than one particle size and shape is used, then the composition will have size and shape distributions corresponding to the size and shape distribution of the particles used to make the composition.

Figure 13:
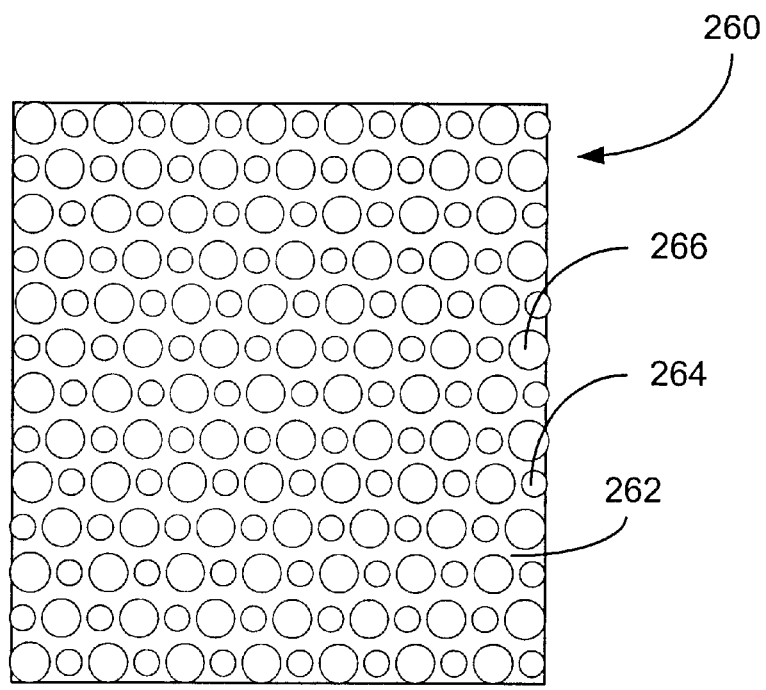
FIG. 13 is a cross-sectional view of a second embodiment of a substantially uniform, highly permeable and/or porous composition of the present invention having different pore sizes.

Referring now to FIG. 13, a second embodiment of an object made from the compositions of the present invention, generally 260, can be seen to include a polymer matrix 262, a first type of pores 264 and a second type of pores 266. Again, the pores 264 and 266 will have a shape and size distribution corresponding generally to the particles size and shape distribution of the particles used to make the composition. It should also be recognized that the pores 254 in the object 250 and the pores 264 and 266 in the object 260 are shown as discrete open areas. However, in reality a number of these open areas may be connected to form interconnected open spaces throughout the objects made from the compositions. Also, it should be recognized that generally as the porosity (void volume/entire volume) approaches 100% (just open space), the number of interconnected open spaces increases.

Figure 14:
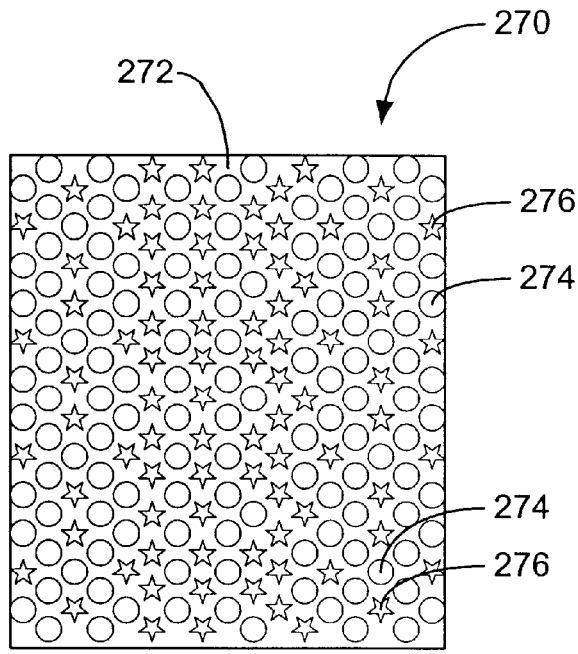
FIG. 14 is a cross-sectional view of a first embodiment of a highly permeable and/or porous composition of the present invention having a differential or variable pore size distribution where the distribution was developed by the application of a radial force.

Referring now to FIG. 14, a third embodiment of an object made from the compositions of the present invention, generally 270, can be seen to include a polymer matrix 272, a first type of pore 274 and a second type of pore 276. The pores 274 and the pores 276 arise from pore-forming particles that have different particle sizes and/or shapes and different densities. Because the particles have different sizes and/or shapes and different densities, the object 270 can be prepared with anisotropic distributions of pore sizes and shapes throughout the composition.

The composition that makes up object 270 can be prepared using a combination of agitation and centripetal force. Using centripetal force in conjunction with agitation, i.e., spinning the composition with agitation, compositions of the present invention can be made with anisotropic distributions of pore sizes and shapes. Depending on when centripetal development is applied, different type of distributions can be prepared. If spinning is started early in the manufacturing process, different density particles can be radially focused. If spinning is then discontinued, then agitation will smear the focusing. By carefully controlling spin speed and duration and agitation onset and duration, compositions with very complex distributions of the pore sizes and shapes can be introduced into the composition.

Figure 15:
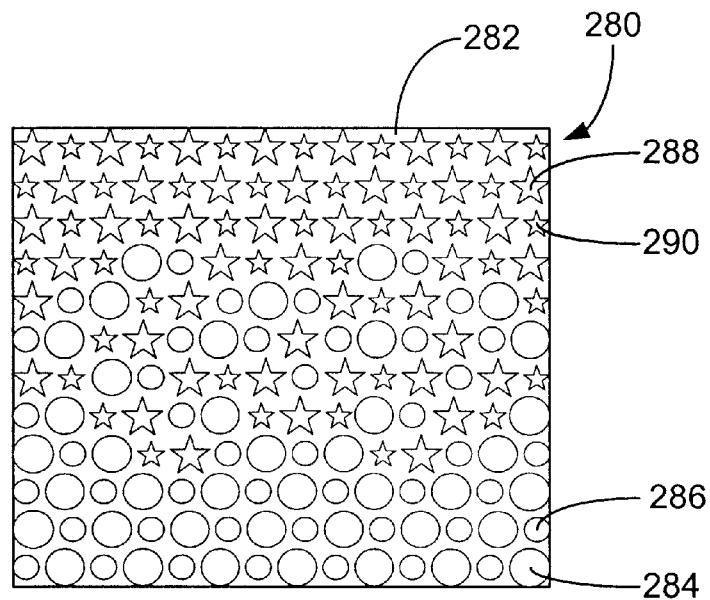
FIG. 15 is a cross-sectional view of a second embodiment of a highly permeable and/or porous composition of the present invention having a differential or variable pore size distribution where the distribution was developed by the application of gravity.

Besides centripetal development (allowing particle segregation by the action of centripetal force on the composition during manufacturing), composition can be developed using gravity or any other applied force. Looking at the object shown in FIG. 15, yet another object made from the compositions of the present invention, generally 280, can be seen to include a polymer matrix 282, a first type of pores 284, a second type of pores 286, a third type of pores 288 and a fourth type of pores 290. The pore-forming particles that left the pores 284 and 286 after leaching, had similar densities, but different particle size distributions (they could have had different shape distribution as well). Similarly, pore-forming particles that left the pores 288 and 290 after leaching, had similar densities, but different particle size distributions. Moreover, the density of the particles responsible for the formation of pores 284 and 286 were more dense than the particles responsible for the formation of the pores 288 and 290. The composition making up object 280 has been gravitionally developed. However, this distribution can be obtained by the action of any applied force on the composition during manufacturing. Again, a judicious application of agitation rate and duration and force application can give rise to any desired void volume distribution.

EXAMPLES

The following examples are include for the sake of completeness of disclosure and to illustrate the methods of making the compositions and composites of the present invention as well as to present certain characteristics of the compositions, but in no way are these examples included for the sake of limiting the scope or teaching of this disclosure.

Example 1

This example illustrates the preparation of a biocompatible, biodegradable polymeric composition useful as a tissues scaffold.

0.125 g of a copolymer of lactic and glycolic acids was dissolved in 3 mL of acetone under constant stirring for 10 min. 2 g of particulate NaCl having a size between about 200 and about 500 µm was placed in a Telfon mold. The polymer solution was added to the vessel. The mixture was agitated using mechanical shaker such as a Vortex under controlled air flow conditions. The air controlled air flow conditions were achieved by placing the agitation unit in a box having flapped hand entry ports and fan operated inlet and filter clad outlets to maintain a constant air flow into and out of the box. Careful control of air flow appears to significantly improve the uniformity and homogeneity of the resulting composition.

After about 3.5 minutes of agitation, an additional 0.5 g of the particulate NaCl was added and agitation was continued. An additional 0.5 g of NaCl was added after about 4 min. and agitation continued. An additional 1.5 g of NaCl was added after about 4.5 min. and agitation continued. At about 8 min., an additional 0.5 g of NaCl was added and agitation was continued for about another min. so that the composition is subjected to about 9 min. of agitation under controlled air-flow conditions.

After addition and agitation, the vessel containing the polymer with the NaCl particles suspended therein, was placed under house vacuum at room temperature for about 24 hrs. The temperature of the vessel was then raised to about 45° C. under house vacuum for an additional about 24 hrs. From the resulting polymer composition, a cylindrical specimen was removed and placed in ultra-pure water for about 72 hrs. The water was replaced every 24 hrs. The water was removed and the specimen was place in a desiccator under vacuum until use.

Example 2

This example illustrates the preparation of nine biodegradable implants according to the process of the present invention.

2.3 grams of 50/50 poly(DL-lactide-co-glycolide) (Birmingham Polymers, Birmingham) with inherent viscosity of 0.69 dl/gm was dissolved in 12.3 mL of pure acetone. The solution was stirred with a 25 mm stir bar in a 28 mm diameter Teflon (DuPont Chemical Company, Wilmington, Del.) beaker until complete dissolution using a Thermix Stirring Hot Plate Model 310T (Fischer Scientific, Pittsburgh, Pa.). In a 40 mm×40 mm×23 mm Teflon well, 9.25 grams of a particular NaCl having particles size between about 0.25 mm to about 0.50 mm was evenly spread. The polymer solution was poured evenly onto the salt in the well.

The mold was then placed in an air-flow chamber, where it was agitated by a Thermolyne Maxi Mix II (Barnstead/Thermolyne, Dubuque, IA) working at maximum power for 6 minutes. The air flow chamber is an enclosed box with variable control fans and filters so that the rate of air passing through the chamber can be controlled. Another 9.25 grams of NaCl was added to the well. The mold was then agitated for an additional 4 minutes. Two grams of salt was then evenly poured over the implant in the well. Agitation was continued for an additional 3 minutes. The mold was left in the air-flow chamber for 24 hours. It was then placed in a heated vacuum at 45° C. and 5000 mTorr for 24 hours. After the 24 hour period, the implants were punched out of the mold with a 10 mm diameter punch. The implants were then placed in distilled water for 72 hours. The water was replaced once daily. The implants were placed in a desiccator at room temperature after they were removed from the water.

Porosity: Porosity is defined as percent void volume and was measured using the Archimedes Principle. First the dry mass of each implant was determined. Then the implant was pre-wet by placing it in ethanol. To force the ethanol into the implant, it was then placed inside a syringe were a negative pressure was created and the air was forced out allowing the ethanol into the implant. The implant was then placed in water, and the same procedures were performed in a syringe with water. The implant was then removed from the water and weighed to determine the wet mass. The implant was then submerged in water and its mass was once again measured. This was the submerged mass. Percent porosity was then calculated using the formula:

$$\%Porosity = (M_{wet} - M_{dry})/(M_{wet} - M_{submerged})$$

A total of six implants were tested in this fashion and the average porosity was 90.83±1.12 percent.

Permeability: Following the fabrication technique described above, six 3×5 mm scaffolds were produced and subjected to tests to quantify their permeability. Permeability (defined as ease or difficulty with which fluid moves past the pores of the scaffold) was measured by using a direct permeation experiment: first a relationship between time and the amount of water which passed through a sample under a known pressure was determined. Next Darcy's law was used to calculated the permeability. The average permeability of the test specimens was 2.43×10–07±1.12 m4/N.s Example 3

This example illustrates the preparation of a 7 mm by 7 mm compositions using a 50:50 copolymer of lactic and glycolic acid.

0.125 grams of a 50:50 a lactic acid/glycolic acid copolymer was dissolved in 3 mL of acetone. The solution was added onto an appropriate amount of sodium chloride particles in a Teflon mold. The mixture was then agitated on a Vortex shaker for 5 minutes under controlled airflow conditions. Shaking was stopped. The composition was then placed under house vacuum for 24 hours. The composition was then placed under heat and vacuum of an additional 24 hours. During the heat and vacuum treatment, the majority to substantially all of the solvent is removed and the particles are allowed to settle due to the action of gravity on the composition. Using an appropriate sized cutter, a cylindrical construct having a diameter of 7 mm and a height of 7 mm was cut from the composition. The construct or plug was placed in ultra pure water for 72 hours to remove the sodium chloride particles, exchanging the water every 24 hours.

Example 4

This example illustrates the preparation of a 7 mm by 7 mm uniform porosity composition using a 50:50 copolymer of lactic and glycolic acid having a non-porous coating applied thereto.

0.125 grams of a 50:50 a lactic acid/glycolic acid copolymer was dissolved in 3 mL of acetone. The solution was added onto an appropriate amount of sodium chloride particles in a Teflon mold. The mixture was then agitated on a Vortex shaker for 5 minutes under controlled airflow conditions. A second portion of sodium chloride was added to the surface of the composition and shaking was continued. The composition was then placed under house vacuum for 24 hours with shaking. The composition was then placed under heat and vacuum of an additional 24 hours with shaking. Using an appropriate sized cutter, a cylindrical construct having a diameter of 7 mm and a height of 7 mm was cut from the composition. The construct or plug was placed in ultra pure water for 72 hours to remove the sodium chloride particles, exchanging the water every 24 hours. The construct was then coated with a non-porous coated of the copolymer by dipping one end of the plug in a 10% by weight solution of the copolymer. The coated plug was then vacuum treated for 24 hours to remove the solvent in the coating.

Example 5

This example illustrates the preparation of compositions having a uniform porosity and/or permeability which are then coated by a non-porous, impermeable coating.

2.3 grams of 50/50 poly(DL-lactide-co-glycolide) (Birmingham Polymers, Birmingham) with inherent viscosity of 0.69 dl/gm was dissolved in 12.3 mL of pure acetone. The solution was stirred with a 25 mm stir bar in a 28 mm diameter Teflon (DuPont Chemical Company, Wilmington, Del.) beaker until complete dissolution using a Thermix Stirring Hot Plate Model 310T (Fischer Scientific, Pittsburgh, Pa.). In a 40 mm×40 mm×23 mm Teflon well, 9.25 grams of a particular NaCl having particles size between about 0.25 mm to about 0.50 mm was evenly spread. The polymer solution was poured evenly onto the salt in the well.

The mold was then placed in an air-flow chamber, where it was agitated by a Thermolyne Maxi Mix II (Barnstead/Thermolyne, Dubuque, IA) working at maximum power for 6 minutes. The air flow chamber is an enclosed box with variable control fans and filters so that the rate of air passing through the chamber can be controlled. Another 9.25 grams of NaCl was added to the well. The mold was then agitated for an additional 4 minutes. Two grams of salt was then evenly poured over the implant in the well. Agitation was continued for an additional 3 minutes. The mold was left in the air-flow chamber for 24 hours. It was then placed in a heated vacuum at 45° C. and 5000 mTorr for 24 hours. After the 24 hour period, the implants were punched out of the mold with a 10 mm diameter punch. The implants were then placed in distilled water for 72 hours. The water was replaced once daily. The implants were placed in a desiccator at room temperature after they were removed from the water.

Once highly permeable scaffolds were made, one side of 3 constructs were dipped in a 2 mm thick PLG/acetone solution for 5 s. The constructs were then dried in the air-flow chamber for 24 hours.

Example 6

This example illustrates the preparation of compositions having a uniform porosity and/or permeability which are then spray coated with a non-porous, impermeable coating.

One side of 3 uniformly permeable constructs of Example 3 were rendered essentially impermeable by spraying an PLG/acetone solution using an atomizer spray gun onto the desired side of the constructs.

Example 7

This example illustrates the preparation of compositions having a uniform porosity and/or permeability through the bulk of the composition and a substantially non-porous, impermeable thin top layer.

2.3 grams of 50/50 poly(DL-lactide-co-glycolide) (Birmingham Polymers, Birmingham) with inherent viscosity of 0.69 dl/gm was dissolved in 12.3 mL of pure acetone. The solution was stirred with a 25 mm stir bar in a 28 mm diameter Teflon (DuPont Chemical Company, Wilmington, Del.) beaker until complete dissolution using a Thermix Stirring Hot Plate Model 310T (Fischer Scientific, Pittsburgh, Pa.). In a 40 mm×40 mm×23 mm Teflon well, 9.25 grams of a particular NaCl having particles size between about 0.25 mm to about 0.50 mm was evenly spread. The polymer solution was poured evenly onto the salt in the well.

The mold was then placed in an air-flow chamber, where it was agitated by a Thermolyne Maxi Mix II (Barnstead/Thermolyne, Dubuque, IA) working at maximum power for 6 minutes. The air flow chamber is an enclosed box with variable control fans and filters so that the rate of air passing through the chamber can be controlled. Another 9.25 grams of NaCl was added to the well. The mold was then agitated for an additional 4 minutes. The mold was left in the air-flow chamber for 24 hours. It was then placed in a heated vacuum at 45° C. and 5000 mTorr for 24 hours. After the 24 hour period, the implants were punched out of the mold with a 10 mm diameter punch. The implants were then placed in distilled water for 72 hours. The water was replaced once daily. The implants were placed in a desiccator at room temperature after they were removed from the water. Nine constructs were produced having one relatively impermeable side (the top side).

Example 8

This example illustrates the preparation of compositions having a uniform porosity and/or permeability through the bulk of the composition and a substantially non-porous, impermeable thin top layer.

2.3 grams of 50/50 poly(DL-lactide-co-glycolide) (Birmingham Polymers, Birmingham) with inherent viscosity of 0.69 dl/gm was dissolved in 12.3 mL of pure acetone. The solution was stirred with a 25 mm stir bar in a 28 mm diameter Teflon (DuPont Chemical Company, Wilmington, Del.) beaker until complete dissolution using a Thermix Stirring Hot Plate Model 310T (Fischer Scientific, Pittsburgh, Pa.). In a 40 mm×40 mm×23 mm Teflon well, 9.25 grams of a particular NaCl having particles size between about 0.25 mm to about 0.50 mm was evenly spread. The polymer solution was poured evenly onto the salt in the well.

The mold was then placed in an air-flow chamber, where it was agitated by a Thermolyne Maxi Mix II (Barnstead/Thermolyne, Dubuque, IA) working at maximum power for 6 minutes. The air flow chamber is an enclosed box with variable control fans and filters so that the rate of air passing through the chamber can be controlled. Another 9.25 grams of NaCl was added to the well. The mold was then agitated for an additional 4 minutes. Two grams of salt was then evenly poured over the implant in the well. The mold was left in the air-flow chamber for 24 hours. It was then placed in a heated vacuum at 45° C. and 5000 mTorr for 24 hours. After the 24 hour period, the implants were punched out of the mold with a 10 mm diameter punch. The implants were then placed in distilled water for 72 hours. The water was replaced once daily. The implants were placed in a desiccator at room temperature after they were removed from the water. Constructs were produced having one relatively impermeable side (the top side).

The porosity and permeability of six compositions were measured following the techniques described above. Permeability was found to be essentially close to zero. Porosity of the impermeable surface was also practically zero.

All United States patents, all foreign patents and all articles cited therein are incorporated herein by reference as if each was incorporated by reference at the time of introduction. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for forming permeable/porous compositions comprising the steps of:
   agitating a mixture comprising at least one polymer and at least one particulate pore-forming agent for a time sufficient to form pores in the mixture, where the pores have a volume greater than a volume of the at least one pore-forming agent; and
   leaching the at least one pore-forming agent from the mixture with a leaching reagent to form a polymer matrix having a void volume greater than the volume of the at least one pore-forming agent in the mixture.

2. The method of claim 1, wherein the mixture further comprises a solvent.

3. The method of claim 1, wherein the agitating step is performed at a temperature above a softening temperature of each polymer in the mixture.

4. The method of claim 1, wherein the at least one pore-forming agent has a density different from a density of the at least one polymer.

5. The method of claim 1, further comprising, before the leaching step, the step of:
   developing a first concentration gradient of the at least one pore-forming agent in the mixture by the action of a first externally applied force so that the polymer matrix has a first concentration gradient of pores across a first cross-sectional profile of the matrix and wherein a density of the at least one pore-forming agent is different from a density of the at least one polymer.

6. The method of claim 2, further comprising the step of:
   subjecting the mixture to a reduced pressure for a time sufficient to remove substantially all of the solvent after the leaching step.

7. The method of claim 2, further comprising the steps of:
   subjecting the mixture to a first reduced pressure for a first period of time after the leaching step; and
   subjecting the mixture to a second reduced pressure at an elevated temperature for a second period of time;
   where the sum of the first and second periods of time is sufficient to remove substantially all of the solvent.

8. The method of claim 1, wherein the mixture comprises a plurality of pore-forming agents.

9. The method of claim 5, wherein the mixture comprises a plurality of pore-forming agents, where each agent has a density different from the other agents and from the at least one polymer and wherein the density of at least one pore-forming agent is greater than the density of the at least one polymer and the density of at least one pore-forming agent is less than the density of the at least one polymer.

10. The method of claim 1, wherein the leaching reagent comprises a solvent in which the at least one pore-forming agent is soluble and in which the matrix is substantially insoluble.

11. A method for forming permeable/porous compositions comprising the steps of:
    combining at least one polymer and at least one particulate pore-forming agent to form a mixture;
    agitating the mixture for a time sufficient to form pores having a volume greater than a volume of the at least one pore-forming agent, where the at least one pore-forming agent is substantially insoluble in the at least one polymer; and
    leaching the at least one pore-forming agent from the mixture with a leaching reagent to form a polymer matrix having a void volume greater than a volume of the at least one pore-forming agent in the mixture.

12. The method of claim 11, further comprising, before the leaching step, the step of:
    developing a gradient of the at least one pore-forming agent in the mixture by the action of an externally applied force so that the polymer matrix has a variation in pore concentration and where a density of the at least one pore-forming agent is different from a density of the at least one polymer.

13. The method of claim 11, wherein the mixture further comprises a plurality of pore-forming agents.

14. The method of claim 12, wherein the mixture comprises a plurality of pore-forming agents and a density of each agent is different from the other agents and different from a density of the at least one polymer and the method further comprises, before the leaching step, the step of:
    developing a multi-dimensional variation in concentrations of the pore-forming agents in the mixture by the action of at least two externally applied forces so that the mixture has a variation in the concentration of each agent in the mixture, where a density of each agent is different from the other agents and different from a density of the at least one polymer and the density of at least one pore-forming agent is greater than a density of the at least one polymer and the density of at least one pore-forming agent is less than the density of the at least one polymer.

15. The method of claim 11, wherein the leaching reagent comprises a solvent in which the at least one pore-forming agent is soluble and in which the matrix is substantially insoluble.

16. The method of claim 1, wherein the mixture comprises a plurality of pore-forming agents and a density of each agent is different from the other agents and different from a density of the at least one polymer and the method further comprises, before the leaching step, the step of:
    developing a multi-dimensional variation in concentrations of the pore-forming agents in the mixture by the action of at least two externally applied forces so that the mixture has a variation in the concentration of each agent in the mixture.

17. The method of claim 13, wherein the each agent has a different density.

18. The method of claim 13, wherein a size or shape of each pore-forming agent is different from a size and shape of the other pore-forming agents.

19. The method of claim 1, wherein the at least one polymer comprises a biocompatible polymer.

20. The method of claim 11, wherein the at least one polymer comprises a biocompatible polymer.

21. The composition of claim 16, wherein the at least one polymer comprises a biocompatible polymer.

22. The method of claim 11, wherein the mixture further comprises a solvent in which the at least one pore-forming agent is substantially insoluble and the method further comprises the step of:
    subjecting the mixture to a reduced pressure at a temperature and for a time sufficient to remove substantially all of the solvent after the leaching step.

23. The method of claim 11, wherein the mixture further comprises a solvent in which the at least one pore-forming agent is substantially insoluble and the method further comprises the steps of:
    subjecting the mixture to a first reduced pressure for a first period of time after the leaching step; and
    subjecting the mixture to a second reduced pressure at an elevated temperature for a second period of time;
    where the sum of the first and second periods of time is sufficient to remove substantially all of the solvent.

* * * * *